(12) United States Patent
Merced et al.

(10) Patent No.: US 10,687,117 B2
(45) Date of Patent: Jun. 16, 2020

(54) SYSTEMS AND METHODS FOR DYNAMICALLY ENABLING AND DISABLING A BIOMETRIC DEVICE

(71) Applicant: Rovi Guides, Inc., San Jose, CA (US)

(72) Inventors: Angel Merced, Wilmington, DE (US); Krista Ramirez, Ardmore, PA (US); Todd Dietz, North Wales, PA (US)

(73) Assignee: Rovi Guides, Inc., San Jose, CA (US)

( * ) Notice: Subject to any disclaimer, the term of this patent is extended or adjusted under 35 U.S.C. 154(b) by 0 days.

(21) Appl. No.: 16/185,434

(22) Filed: Nov. 9, 2018

(65) Prior Publication Data

US 2019/0200085 A1 Jun. 27, 2019

Related U.S. Application Data

(63) Continuation of application No. 15/850,244, filed on Dec. 21, 2017, now Pat. No. 10,158,919.

(51) Int. Cl.
  *G06F 3/00* (2006.01)
  *G06F 13/00* (2006.01)
  (Continued)

(52) U.S. Cl.
  CPC ....... *H04N 21/4756* (2013.01); *A61B 5/0077* (2013.01); *A61B 5/02438* (2013.01); *A61B 5/165* (2013.01); *A61B 5/486* (2013.01); *G16H 20/70* (2018.01); *G16H 40/40* (2018.01); *G16H 50/30* (2018.01); *G16H 50/50* (2018.01); *G16H 50/70* (2018.01); *H04L 63/0861* (2013.01); *H04L 63/102* (2013.01); *H04N 21/252* (2013.01); *H04N 21/25891* (2013.01); *H04N 21/42201* (2013.01); *H04N 21/44218* (2013.01); *H04N 21/4532* (2013.01); *H04N 21/4667* (2013.01); *H04N 21/4668* (2013.01); *H04N 21/4755* (2013.01); *H04N 21/4788* (2013.01); *H04N 21/8456* (2013.01); *A61B 5/0015* (2013.01)

(58) Field of Classification Search
  CPC ............ H04N 21/4756; H04N 21/252; H04N 21/25891; H04N 21/42201; H04N 21/44218; H04N 21/4532; H04N 21/4668; H04N 21/4755; H04N 21/4788; G16H 40/40; A61B 5/486; H04L 63/0861
  See application file for complete search history.

(56) References Cited

U.S. PATENT DOCUMENTS

| 9,525,912 | B1 * | 12/2016 | Israelian | G06F 16/245 |
| 2009/0089833 | A1 * | 4/2009 | Saito | H04H 60/33 725/38 |

(Continued)

OTHER PUBLICATIONS

International Search Report and Written Opinion dated Mar. 4, 2019 in PCT/US2018/066154.

*Primary Examiner* — Mulugeta Mengesha
(74) *Attorney, Agent, or Firm* — Haley Guiliano LLP

(57) ABSTRACT

Systems and methods are described to address deficiencies in conventional biometric devices by dynamically enabling and disabling a biometric device based on the content the user is viewing. The media guidance application may utilize a device enablement rule, which has content criteria. If the content criteria is satisfied, the media guidance application may enable or disable a biometric device in accordance with the device enablement rule.

18 Claims, 10 Drawing Sheets

(51) Int. Cl.
*H04N 5/445* (2011.01)
*H04N 21/475* (2011.01)
*G16H 40/40* (2018.01)
*A61B 5/00* (2006.01)
*H04L 29/06* (2006.01)
*H04N 21/25* (2011.01)
*H04N 21/258* (2011.01)
*H04N 21/422* (2011.01)
*H04N 21/442* (2011.01)
*H04N 21/45* (2011.01)
*H04N 21/466* (2011.01)
*H04N 21/4788* (2011.01)
*A61B 5/16* (2006.01)
*A61B 5/024* (2006.01)
*G16H 50/30* (2018.01)
*G16H 50/70* (2018.01)
*G16H 50/50* (2018.01)
*H04N 21/845* (2011.01)
*G16H 20/70* (2018.01)

(56) References Cited

U.S. PATENT DOCUMENTS

| | | |
|---|---|---|
| 2012/0324493 A1 | 12/2012 | Holmdahl et al. |
| 2014/0223462 A1 | 8/2014 | Aimone et al. |
| 2016/0182955 A1* | 6/2016 | Klappert ............ H04N 21/4668 725/14 |
| 2017/0257410 A1 | 9/2017 | Gattis et al. |
| 2018/0008194 A1* | 1/2018 | Boesen ................ H04R 1/1091 |
| 2018/0324490 A1* | 11/2018 | Anderson ........ H04N 21/42201 |
| 2018/0373717 A1* | 12/2018 | Eriksson ................ G06F 17/16 |

* cited by examiner

SYSTEMS AND METHODS FOR DYNAMICALLY ENABLING AND DISABLING A BIOMETRIC DEVICE

CROSS-REFERENCE TO RELATED APPLICATION

This application is a continuation of U.S. patent application Ser. No. 15/850,244, filed Dec. 21, 2017, (now allowed), which is hereby incorporated by reference herein in its entirety.

BACKGROUND

Biometric devices are common technology, used to monitor various characteristics of a user such as the user's physical activity or the user's organic function and vitals. However, the abundance of biometric devices and, as an extension, the abundance of measurements from biometric devices can be overwhelming for a user. In many cases, the device consumes a lot of resources to collect data that the user does not need, or will never access. Since biometric devices can be wearable devices, constant data acquisition can lead to quicker battery drains and overuse of the processor. This large amount of information may also be excessive and can breach the user's privacy (e.g., the biometric device may collect data when the user does not wish for data to be collected).

SUMMARY

Accordingly, systems and methods are described to address deficiencies in conventional biometric devices by dynamically enabling and disabling a biometric device based on the content the user is viewing. Suppose that a user is using a biometric device (e.g., Fitbit band) to track physical activity and vitals. For example, the Fitbit band may monitor the user's heart rate, sleeping patterns, steps taken, calories, etc. Rather than continuously collecting data, a media guidance application may be used to disable and enable data collection of the Fitbit band based on the content that the user is viewing. For example, the media guidance application may detect that the user is viewing a horror movie (e.g., "The Conjuring"), which features a scene presenting a jump scare. The scene may be associated with an enablement rule that causes the Fitbit band to begin tracking the user's heart rate. Once the scene starts, the Fitbit may start collecting heart rate measurements. Based on the user's reaction, the media guidance application may also provide a content recommendation. For example, if the user's heart rate did not change, it is possible that the user was not scared by the scene. Therefore, the media guidance application may recommend a scarier movie.

The media guidance application may determine that a user is accessing content on user equipment (e.g., set-top box, laptop, smartphone). Suppose that the user is viewing the horror movie "The Conjuring." It should be noted that the content being accessed by the user may be any media including, but not limited to, videos, audio, graphics and/or games.

The media guidance application may retrieve a device enablement rule associated with the content. The media guidance application may retrieve metadata associated with the content being accessed. The metadata may include device enablement rules associated with the content. For example, each scene of the movie may be associated with a device enablement rule created by the content provider. Accordingly, the metadata may include a list of scenes that details the name of a scene, the time the scene starts in the movie, information about the content in the scene, a device enablement rule, and the rule's compatibility with various biometric devices. Suppose that the media guidance application determines that "The Conjuring" has seventy scenes. Furthermore, based on the metadata of the movie, the media guidance application determines that scene two has a device enablement rule associated with the Fitbit band and various heart rate monitors. The device enablement rule may prompt the biometric device to monitor the user's heart rate throughout the duration of playback of scene two. In addition, the device enablement rule may contain information about an expected biometric response (e.g., an exciting scene in a movie may be expected to cause an accelerated heart rate).

The media guidance application may determine whether the content currently being accessed satisfies the device enablement rule. As previously mentioned, the metadata of the content may include information about the device enablement rule, and the rule's compatibility with various biometric devices. More specifically the compatibility information may include a list of biometric devices that are associated with the device enablement rule. It should be noted that the biometric device may be any device or smart technology that can monitor a characteristic of a user (e.g., facial expressions, movement, sounds, stress levels, daily habits, vitals, body temperature, etc.) For example, the biometric device may be an imaging device (e.g., Microsoft Kinect) which may track the user's expressions, pupil dilation, eye movements, etc. Similarly, the biometric device may be a smart speaker (e.g., Google Home, Amazon Echo, etc.) that may monitor sounds made by the user, such as talking, laughing, crying, etc. In addition, the media guidance application may determine that the user has begun viewing scene two of "The Conjuring." Furthermore, the media guidance application may determine that the user is using a biometric device (e.g., Fitbit band) that is in the list of biometric devices. In response, the media guidance application may determine that the content currently being accessed satisfies the device enablement rule.

In response to determining that the content currently being accessed satisfies the device enablement rule, the media guidance application may temporarily activate a biometric device associated with the user while the content currently being accessed continues to satisfy the device enablement rule. For example, the media guidance application may keep the Fitbit's heart rate monitoring feature active while scene two is being generated for display to the user. Suppose that the device enablement rule is associated with a smart speaker (e.g., Google Home) to collect voice samples of the user during scene two (e.g., when a jump scare appears). During playback of scene two, the media guidance application may enable audio collection of the Google Home. Accordingly, if the user screams or reacts audibly, the Google Home may record the audio. In another scenario, suppose that the device enablement rule is associated with a motion tracker for monitoring the movement of the user. The motion tracker may incorporate a camera, such as in a smartphone, a Microsoft Kinect, a webcam, etc. In response to the playback of scene two, the media guidance application may enable the motion tracker to monitor various features such as the user's movements, facial expressions, interaction with the user's surroundings, etc. For example, if the user is accessing "The Conjuring" on his/her smartphone, the camera on the smartphone may be enabled to monitor the eye movement of the user. This information can indicate whether the user looked away from the screen in response to the jump scare or closed his/her eyes. In some embodiments, the media guidance application may label the time when the device enablement rule was satisfied as the start time and wait for an end time, which is the time when the device enablement rule will stop being satisfied (e.g., at the end of scene two). Once the end time is reached, the media guidance application may deactivate the biometric device. Deactivating the device may simply involve stopping the device from collecting data until further instruction from the user or media guidance application. In some cases, deactivating may involve sending the biometric device into sleep mode, a lower power mode, or completely shutting the power down. It should be noted that the end time may not take place within the time period that the user accesses the content (e.g., media asset). For example, the device enablement rule may enable a biometric device for a long period of time. Suppose that the user is listening to a podcast about healthy eating. The podcast may be associated with a device enablement rule that enables the user's smartphone or smart speaker to track the user's eating habits over the course of two weeks, starting from when the user stops listening to the podcast. Accordingly, the user's smartphone may prompt the user to enter his/her dietary information on a daily/weekly basis; the user's smart speaker may request this information verbally.

The media guidance application of the biometric device may measure a biometric response of the user to the content currently being accessed while the biometric device is activated. Suppose that the Fitbit acquires a set of heart rate measurements every two minutes and that scene two is ten minutes in duration. While the Fitbit's heart rate monitoring feature is activated for the ten-minute duration of scene two, the Fitbit may collect six sets of heart rate measurements. In the example given of a smart speaker, a Google Home may begin collecting an audio sample for the duration of scene two.

The media guidance application may generate a content recommendation based on the measured biometric response. Suppose that scene two is a horror scene with multiple jump scares. The biometric response may be the set of heart rate measurements acquired by the Fitbit. The device enablement rule may indicate that the expected biometric response should be in a heart rate range of 90-100 beats per minute. The media guidance application may refer to a biometrics database that includes information about different levels of biometric responses. The biometrics database may have a heart rate table classifying various heart rate levels. For example, 60-80 beats per minute may be classified as a normal heart rate, whereas 80-100 beats per minute may be classified as an accelerated heart rate, in the heart rate table. The media guidance application may determine that the average heart rate from the six sets of measurements is 72 beats per minute. Based on the heart rate table, the media guidance application may therefore determine that the user's heart rate is in the normal heart rate class and is not in the expected "accelerated" class, as indicated in the expected biometric response. As a result, the media guidance application may search for content that can accelerate the user's heart rate. For example, the user may not find the scenes in "The Conjuring" scary and was thus unaffected by scene two. The media guidance application may determine that the genre of the user's accessed content "The Conjuring" is horror. Accordingly, the media guidance application may determine that the user should be recommended content from the horror genre that is considered scarier. In some embodiments, the media guidance application may provide supplemental content while the user is accessing content, in order to alter the user's biometric response. For example, the media guidance application may activate an external component such as a Google Home device owned by the user, to generate sounds associated with horror. The media guidance application may also overlay a scary character jumping out at the user in virtual reality or augmented reality. While the supplemental content is being provided, the media guidance application may monitor for changes in the user's biometric response (e.g., increased heart rate).

In some aspects, the media guidance application may determine that a user is accessing content on user equipment. In some embodiments, the content includes at least one of a linear media asset (e.g., television broadcast sports event), an on-demand media asset (e.g., a movie), and social chatter on a social platform associated with the user (e.g., a forum/discussion). Suppose that the user is viewing the horror movie "It: Chapter One," an on-demand media asset, on his/her set-top box.

The media guidance application may retrieve a device enablement rule associated with the content. The media guidance application may retrieve metadata associated with the content being accessed. The metadata may include device enablement rules associated with the content. For example, the media guidance application may determine a device enablement rule that prompts biometric devices to collect heart rate measurements from the user.

In some embodiments, the media guidance application may generate a new device enablement rule. For example, suppose that the content provider has not added a device enablement rule to the metadata of the content. The media guidance application may identify popular content, characters, topics, people, places, etc. by referring to social media (e.g., trending on Twitter). The media guidance application may also identify items in the user profile that the user prefers (e.g., content, characters, actors, artists, places, etc.). These preferences may be explicitly stated (e.g., the user indicates that his/her favorite actor is Tom Hanks), or implicitly (e.g., the user's viewing history indicates that the user has viewed several movies featuring Tom Hanks). In response, the media guidance application may generate a device enablement rule with content criteria that corresponds to popularity and/or the user profile.

In some embodiments, the media guidance application may allow the user to create device enablement rules. For example, the media guidance application may allow the user to access a list of device enablement rules in the user profile and allow the user to manually add device enablement rules. The user may enter the device enablement rule and the media guidance application may parse the user-generated device enablement rule to ensure that the user's device enablement rule is valid. For example, if a user creates the device enablement rule for measuring heart rate and associates it with a pedometer which cannot measure heart rate, the media guidance application may prompt the user that the user-generated device enablement rule is not valid.

The media guidance application may determine content criteria specified by the device enablement rule. A device enablement rule may be programmed with "if-else" logic. For example, the device enablement rule may be structured as "IF [Criteria 1] and/or [Criteria 2] . . . and/or [Criteria N], THEN [RESPONSE A1] and/or [RESPONSE A2] . . . and/or [RESPONSE AN]; ELSE [RESPONSE B1] and/or [RESPONSE B1] . . . and/or [RESPONSE BN]." In this structure, if a combination of the criteria, as established by the content provider or user, is met, the media guidance application will execute the respective response combination from the A set (e.g., A1, A2, etc.). If the combination of the criteria is not met, the media guidance application will execute the respective response combination from the B set (e.g., B1, B2, etc.). Suppose that the content provider established the device enablement rule states "IF Pennywise the Clown appears in a scene, THEN enable the biometric device and prompt the biometric device to take a heart rate measurement; ELSE disable the biometric device." Suppose that the biometric device is the Fitbit. The content criteria in this device enablement rule is the appearance of Pennywise the Clown, a character in "It: Chapter One," in a scene of the movie.

The media guidance application may retrieve metadata associated with the content being accessed on the user equipment that matches the content criteria. The media guidance application may refer to the metadata associated with the movie to determine the characters that appear in the movie at various playback positions (e.g., Pennywise the Clown). The media guidance application may also use computer vision to identify objects on the screen and classify whether the object is Pennywise the Clown or not, using a reference image of Pennywise the Clown (e.g., retrieved from the Internet). The media guidance application may refer to the subtitles of the movie to determine when Pennywise the Clown is mentioned in the movie. The media guidance application may also analyze the audio of the movie and utilize natural language processing to identify the voice of Pennywise the Clown, using a reference voice model of Pennywise the Clown (e.g., retrieved from the Internet). Using any combination of these processes, the media guidance application may identify the appearance of Pennywise the Clown and determine that the content criteria is met.

In some embodiments, the device enablement rule may specify the playback positions in which Pennywise the Clown appears in the movie. For example, the device enablement rule may state "IF playback is at position 0:12:57 or 0:50:12 or 1:24:23, THEN enable the biometric device and prompt the biometric device to take a heart rate measurement; ELSE disable the biometric device." The content criteria in this case points to specific playback positions in the movie, such as 12 minutes and 57 seconds from the start (e.g., 0:12:57). Once playback to the user reaches this point, the content criteria may be satisfied.

The media guidance application may compare the retrieved metadata to a condition specified by the device enablement rule, to determine whether the content being accessed on the user equipment satisfies the device enablement rule. For example, if the user is on playback position 0:12:57, the media guidance application may determine that the content criteria of the device enablement rule is satisfied. In contrast, if the user is on playback position 0:05:11, the media guidance application may determine that the content criteria of the device enablement rule is not satisfied.

The media guidance application may identify a biometric device of the user associated with the device enablement rule. As previously mentioned, the device enablement rule may be retrieved from the metadata of the content. The metadata may also include information about the biometric devices that the user possesses. For example, the media guidance application may determine, from the metadata, that the biometric device associated with the device enablement rule (e.g., to measure heart rate) and possessed by the user include a Samsung Gear, a Fitbit band, and a portable heart rate monitor.

In some embodiments, the media guidance application may determine whether the biometric device is being used by the user. For example, the media guidance application may communicate with the user's Fitbit band to determine whether the user is wearing the band. Biometric devices usually have a built-in sensor to determine whether the user is in contact with the biometric device. If the user is not near the Fitbit band (e.g., user is viewing the movie in the living room and the biometric device is in the user's bedroom), the media guidance application may determine that the device does not satisfy the device enablement rule because it cannot physically measure the user's heart rate if the content criteria is met.

The media guidance application may temporarily activate the identified biometric device while the content being accessed continues to satisfy the device enablement rule. Returning to the overarching example, the media guidance application may identify that the user is wearing his/her Fitbit band. In addition, the media guidance application may determine that Pennywise the Clown has appeared in a scene being viewed by the user. In response, the media guidance application may determine that the content criteria of the device enablement rule have been satisfied, and may enable the biometric device. The user's Fitbit may remain enabled until Pennywise the Clown exits the scene.

The media guidance application may measure a biometric response of the user to the content being accessed while the biometric device is activated. For example, while Pennywise the Clown is in the scene being viewed by the user, the media guidance application may ensure that the user's Fitbit band is active, and is collecting the user's heart rate. In some embodiments, the media guidance application may store this biometric response (e.g., heart rate values organized with time stamps). The media guidance application may determine that during the duration in which the Fitbit was enabled, the average heart rate of the user was 111 beats per minute.

The media guidance application may then generate a content recommendation based on the measured biometric response. Suppose that in a certain scene, Pennywise the Clown appears. Metadata associated with the device enablement rule may indicate that the expected biometric response should be in a heart rate range of 90-100 beats per minute. The media guidance application may refer to a biometrics database that includes information about different levels of biometric responses. As previously mentioned, the biometrics database may have a heart rate table classifying various heart rate levels. For example, 80-100 beats per minute may be classified as an accelerated heart rate and 100-120 may be classified as very accelerated, in the heart rate table. Based on the heart rate table, the media guidance application may therefore determine that the user's heart rate is in the "very accelerated" heart rate class and is not in the expected "accelerated" class, as indicated in the expected biometric response.

In some embodiments, if the user's biometric response increases beyond a threshold (e.g., 140 beats per minute), the media guidance application may stop playback of the content being accessed by the user as a safety measure. In some embodiments, the media guidance application may search for content that can slow down the user's heart rate. The media guidance application may determine that the genre of the user's accessed content "It: Chapter One" is horror. Accordingly, the media guidance application may determine that the user should be recommended content from the horror genre that is considered less scary. The media guidance application may refer to the Internet to search for horror movies with device enablement rules associated with a "slightly-accelerated heart rate" expected biometric response. Once the media guidance application has identified a list of content associated with a "slightly accelerated heart rate," the media guidance application may search for content in the list of content that is associated with the horror genre in their respective metadata. Suppose that the media guidance application identifies the movie "The Conjuring" which features scenes with device enablement rules associated with maximum "slightly accelerated" heart rates. The media guidance application may generate for display, the recommendation, after the viewer has stopped watching "It: Chapter One," recommending "The Conjuring." In some embodiments, the media guidance application may generate for display, the recommendation, on a second display screen (e.g., the user's smartphone).

In some embodiments, the media guidance application may remove portions from the content being accessed by the user, in order to alter the user's biometric response. For example, the media guidance application may determine that the user's biometric response is a very high heart rate in response to Pennywise the Clown's appearance. Due to this, the media guidance application may block out Pennywise the Clown using computer vision (e.g., segmentation and classification) or replace Pennywise the Clown with a less scary image. The media guidance application may also skip scenes that will feature Pennywise the Clown. The media guidance application may then monitor whether the user's heart rate decreases in response to the removal of portions.

In some embodiments, the media guidance application may search a social network based on an identifier of the content to identify a plurality of communications associated with the content. The identifier of the content may be any representation of the content such as the content's name (e.g., "It: Chapter Name"), common name (e.g., "It"), genre (e.g., horror), creator (e.g., artist, production house, director, etc.), characters, cast, artwork, and/or sound. Accordingly, the media guidance application may search for "Pennywise the Clown" on a social network such as Facebook, in order to identify a plurality of communications associated with "Pennywise the Clown." The plurality of communications may include posts, comments, messages, acknowledgments (e.g., likes, reactions, etc.), videos, photos, audio clips, etc.

The media guidance application may then identify a number of the communications that were received by the social network within a threshold period of time of a progress position of the content. The threshold period of time may be a window of time before and/or after the progress position of the content. The progress position represents a discrete point in the content and may include, but is not limited to, the playback position of a video/audio or a slide number in a slideshow of images and text. Suppose that the progress point is 12 min 50 seconds into the movie "It: Chapter One" and the threshold period of time is ten minutes. The media guidance application may thus only consider communications that were received by the social network, Facebook, between 7 min 50 seconds and 17 min 50 seconds. While accessing "It: Chapter One," a first user (e.g., the user's friend) may post a comment on a social network. The media guidance application on the friend's device may determine that the friend is accessing "It: Chapter One" and add the friend's progress point as metadata to the friend's communication. When the media guidance application on the user's device identifies communications, the media guidance application may retrieve the metadata of the communication to determine whether the communication's progress point is within the threshold period of time. In the case where the user is accessing content being broadcasted, the media guidance application may determine the transmission time of the content and consider the progress point with respect to the transmission time. For example, if "It: Chapter One" is broadcasted (e.g., transmitted to a plurality of users simultaneously) on HBO on Nov. 1, 2017 at 8:00 pm, and the progress point is 12 min 50 seconds into the movie, the media guidance application may consider commercial times and content version in order to determine that the progress point time is 8:15 pm. Thus, the threshold period of time may be any ten-minute window around 8:15 pm (e.g., 8:12 pm and 8:22 pm). As a result, the media guidance application may consider communications that were received by a social network during that time.

The media guidance application may then determine whether the number of the communications exceeds a threshold value. For example, the media guidance application may count the number of communications that were received within a threshold period of time by various social networks (e.g., Facebook, Twitter, Instagram, Reddit, etc.) and are associated with the identifier of the content. Suppose that the media guidance application identifies 10,000 communications. In some embodiments, the user may also limit the communications to those posted by the user's friends. In this case, the media guidance application may identify 50 communications. The media guidance application may retrieve a threshold value from the user profile. The threshold value may represent a minimum number of communications needed to classify a portion of the content as popular (e.g., a famous scene in the movie). Suppose that the threshold value is 20, a number less than the number of communications associated with the user's friends. As a result, the media guidance application may detect that a portion of the content corresponding to the progress position of the content is popular. In determining that the portion is popular, the media guidance application may generate a device enablement rule associated with the portion if one does not already exist.

In order to establish when the portion starts and when the portion ends (e.g., to determine a playback window in which the device enablement rule is satisfied), the media guidance application may store a start time and an end time of the portion of the content. The start time may be the first time of the window of time formed by the threshold period of time around the progress point. The end time may the last time of the window of time formed by the threshold period of time around the progress point. For example, if the progress point is 12 min 50 seconds, and the threshold period of time is ten minutes, the start time may be 7 min 50 seconds and the end time may be 17 min 50 seconds. In terms of transmission time (e.g., content began transmission at 8:00 pm on HBO), the start time may be 8:08 pm and the end time may be 8:18 pm.

The media guidance application may then detect that a current progression point of the content being accessed corresponds to the start time. For example, the media guidance application may determine that the current progression point of the content (e.g., 12 minutes 50 seconds) corresponds to the start time and is within the threshold period of time. The media guidance application may temporarily activate the biometric device while the current progression point is between the start time and the end time. For example, the media guidance application may communicate with the user's Fitbit band to enable the Fitbit's heart rate measuring feature at the start time. Once the current progression point has reached the end time, the media guidance application may communicate with the user's Fitbit band to disable the Fitbit's heart rate measuring feature.

In some embodiments, the media guidance application may retrieve from the device enablement rule, a set of biometric devices specified in the device enablement rule. For example, the media guidance application may retrieve metadata associated with the device enablement rule. The metadata may include a set of biometric devices that the device enablement rule specifies. For example, the set of biometric devices associated with the device enablement rule that measures heart rate may include Fitbit bands, Samsung Gear, and a portable heart rate monitor.

The media guidance application may then retrieve a list of biometric devices associated with the user. As previously mentioned, the media guidance application may refer to the user profile to identify biometric devices that the user has access to, or is associated with the user. For example, the media guidance application may determine that the user is associated with a Fitbit band, a Samsung Gear, and a pedometer. The media guidance application may then compare the list of biometric devices associated with the user with the set of biometric devices specified in the device enablement rule. For example, the media guidance application may determine that the device enablement rule is associated with the Fitbit band and the Samsung Gear, two devices that the user is associated with. However, the media guidance application may also determine that the user is not associated with a portable heart rate monitor, and the device enablement rule is not compatible with the pedometer.

The media guidance application may select as the identified biometric device, one or more of the biometric devices in the list that matches one or more of the biometric devices in the set of biometric devices. For example, the media guidance application may select the Fitbit band and the Samsung Gear because they appear in both the list and the set of biometric devices. In the case where the user does not have access to any biometric device associated with the device enablement rule, the media guidance application may determine the most popular biometric device from the set of biometric devices. For example, the media guidance application may refer to the biometrics database, and determine that a majority of the users use the Fitbit band in order to measure heart rate. In response, the media guidance application may retrieve a list of vendors that sell the Fitbit band, and recommend purchasing the Fitbit band to the user.

In some embodiments, the media guidance application may determine a type of content being accessed by the user equipment. The type of content may be the medium in which the content is presented. For example, the content may be a video, an audio clip, an e-book, an image, a game, etc. The media guidance application may select as the device enablement rule, a given device enablement rule of a plurality of device enablement rules that corresponds to the type of content being accessed. For example, the user may be able to access the content "It: Chapter One" in various types. These types include a video of the movie, an audiobook, an e-book of the original story written by Stephen King, or a comic featuring various graphics. Depending on the type of content, the device enablement rules may vary. For example, for a video, the device enablement rule may activate a biometric device in response to determining that Pennywise the Clown has appeared in a scene. For the audiobook, a device enablement rule may activate whenever a voice actor portraying Pennywise the Clown speaks.

In some embodiments, the media guidance application may determine that the content being accessed satisfies the device enablement rule, occurs at a first progression point in the content. If a user is accessing "It: Chapter One" in the form of an audiobook, the media guidance application may retrieve a device enablement rule that states "IF the voice actor of Pennywise the Clown speaks, THEN enable the biometric device and measure the user's heart rate; ELSE disable the biometric device." The media guidance application may use voice recognition method (e.g., natural language processing) to identify that the voice actor of Pennywise the Clown begins talking 12 minutes and 50 seconds from the start of the content. The media guidance application may also refer to metadata associated with the audiobook that indicates the times at which various voice actors speak. If the user's current playback position is the first progression point, the media guidance application may check whether the device enablement rule is satisfied. Suppose that the user's first progression point is 12 minutes 50 seconds. The media guidance application may determine that the device enablement rule is satisfied. The media guidance application may monitor additional metadata of the content accessed by the user equipment corresponding to a second progression point later than the first progression point. For example, the media guidance application may determine that the use has reached a second progression point (e.g., 13 minutes 35 seconds). At that point, the media guidance application may monitor the metadata associated with the audiobook to determine the voice actors that are speaking during the second progression point. Suppose that the voice actor for Pennywise the Clown stops speaking at the second progression point.

The media guidance application may then compare the additional metadata to the condition specified by the device enablement rule to determine whether the content being accessed on the user equipment at the second progression point satisfies the device enablement rule. If the device enablement rule measures heart rate when the voice actor of Pennywise the Clown speaks, the media guidance application may determine that the voice actor stops speaking at the second progression point. As a result, the device enablement rule is not satisfied and the media guidance application may deactivate the identified biometric device. For example, if the Fitbit band of the user begins taking heart rate measurements from the first progression point, the media guidance application may communicate with the Fitbit band in order to deactivate the Fitbit band. As a result, the Fitbit band will stop taking heart rate measurements.

In response to determining that the device enablement rule is satisfied, the media guidance application may monitor additional metadata of the content accessed by the user equipment corresponding to a third progression point later than the second progression point. For example, the media guidance application may wait an additional period of time until the user reaches the third progression point (e.g., 15 minutes 2 seconds). Once the user has reached the third progression point, the media guidance application may access metadata associated with the third progression point, such as the name(s) of the voice actors speaking at the third progression point. This serves the purpose of determining a point at which the device enablement rule is no longer satisfied.

In some embodiments, the media guidance application may retrieve an average biometric response of a plurality of users to the content being accessed at the first progression point. For example, the media guidance application may refer to a remote server that stores biometric responses of various users. The remote server may include a biometrics database that is organized based on various measurements and biometric devices. For example, the biometrics database may include heart rate measurements of various users. The heart rate measurements may be associated with content, progression points, and other details (e.g., biometrics) about users such as age and weight. The media guidance application may retrieve the heart rate measurements for a plurality of users listed in the biometrics database that accessed "It: Chapter One." More specifically, the media guidance application may determine whether the biometric response is associated with the first progression point. If so, the media guidance application may determine the average biometric response. For example, if the media guidance application retrieves heart rate measurements for 10,000 users associated with "It: Chapter One" (e.g., audiobook) at the first progression point (e.g., 12 minutes 50 seconds), the media guidance application may determine that the average heart rate is 82 beats per minute.

The media guidance application may compare the biometric response of the user to the average biometric response. Suppose that the biometric response of the user at the first progression point was 80 beats per minute. The media guidance application may rely on a response threshold to compare the user's biometrics response with the average biometrics response. The response threshold represents a range within which the biometric response may correspond. For example, the response threshold for heart rate measurements may be 5 beats per minute. Therefore, if the biometric response of the user is plus or minus 5 beats per minute within range of the average biometric response (e.g., between 77 beats per minute and 87 beats per minute), the media guidance application may determine that the biometric response corresponds to the average biometric response. In some cases, the response threshold is determined by a percentage difference. For example, the response threshold may be 2%. Therefore, the media guidance application may determine that the range of the average heart rate is 2% plus or minus the heart rate (e.g., 2% of 82 is 1.64 and thus the range is between 82−1.64 beats per minute and 82+1.64 beats per minute).

The media guidance application may then identify a group of users who experienced an average biometric response to the content being accessed at the first progression point that corresponds to the biometric response of the user. For example, the media guidance application may determine that of the plurality of 10,000 users identified, 2,000 users experienced a biometric response that also corresponds to the user's biometric response. More specifically, 2,000 users have a biometric response that is within the response threshold of the user. If the user's biometric response is 80 beats per minute and the response threshold is 2 beats per minute, the media guidance application may identify users with an average biometric response between 78 and 82 beats per minute.

The media guidance application may select as the content recommendation, a media asset that corresponds to a group profile associated with the group of users (e.g., the users with an average biometric response between 78 and 82 beats per minute). For example, the media guidance application may determine that out of the 10,000 users identified, 2,000 users have biometric responses corresponding to the user's biometric response. The media guidance application may classify the 2,000 users under a group profile. For example, the media guidance application may access the user profiles of the respective users to determine commonalities of interest (e.g., favorite movies, most accessed media asset, etc.). Based on this information, the media guidance application may recommend a media asset, which a majority of the identified users have accessed, to the user.

In some embodiments, the media guidance application may identify a disorder related to a lack of a typical biometric response to content that matches the content criteria, wherein the media asset relates to the disorder. Suppose that the heart rate of the user, in response to accessing content at the first progression point, rises to 140 beats per minute. In comparison to the average heart rate of the users identified in (e.g., 82 beats per minute), the media guidance application may determine that the user's heart rate is abnormally high. In response, the media guidance application may identify a heart disorder associated with very high heart rates. The media guidance application may refer to the biometrics database to identify disorders associated with the user's abnormal biometric response. The biometrics database may include names of disorders, definitions, and associated values of biometric responses to the disorders, expected biometric responses, and content attributes.

The media guidance application may alert another user associated with the user about the disorder. The media guidance application may refer to the user profile to identify emergency contacts selected by the user. For example, the user may indicate his/her parents as emergency contacts. In response to determining an abnormal biometric response, the media guidance application may send a message to the parents of the user indicating a potential risk for the identified disorder. The message may include, but is not limited to, a text message, an email, a social media message, or a computer voice-generated phone call.

The media guidance application may also monitor treatment progress of the disorder of the user by detecting a different biometric response of the user to additional content that matches the criteria at a subsequent time. For example, the media guidance application may increase the frequency of heart rate measurements by creating device enablement rules that measure heart rate. The media guidance application may recommend content similar to the content the user accessed to compare the difference in biometric responses. For example, the media guidance application may identify that "The Conjuring" is a horror movie with similar average biometric responses as "It: Chapter One," based on the biometrics database. If the user accesses "The Conjuring," the media guidance application may compare the biometric response of user to scenes in "The Conjuring" to scenes in "It: Chapter One." If the user's heart rate is less in the former, the media guidance application may determine that the user's disorder has lessened in severity. If the user's heart rate is in the normal range again, the media guidance application may determine that the user's heart rate is no longer abnormal.

It should be noted that the systems, methods, apparatuses, and/or aspects described above may be applied to, or used in accordance with, other systems, methods, apparatuses, and/or aspects described in this disclosure.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which.

DETAILED DESCRIPTION

Figure 1A:
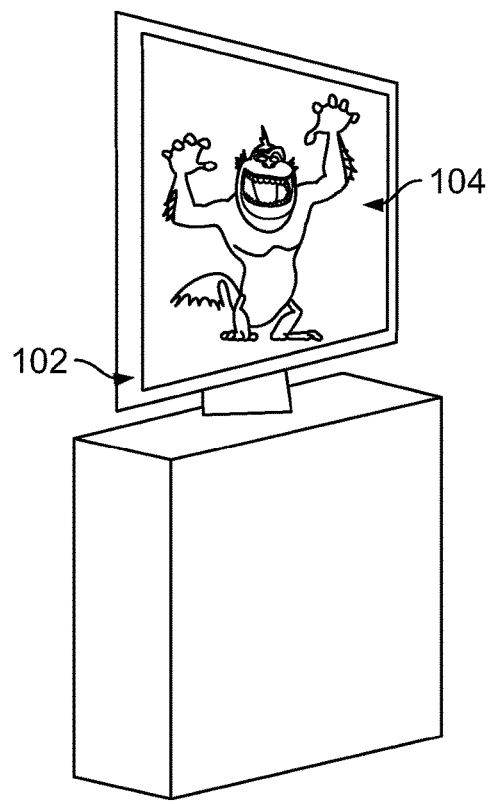
FIGS. 1A and 1B show illustrative examples of scenarios for dynamically enabling and disabling a biometric device, in accordance with some embodiments of the disclosure.
Figure 1A:
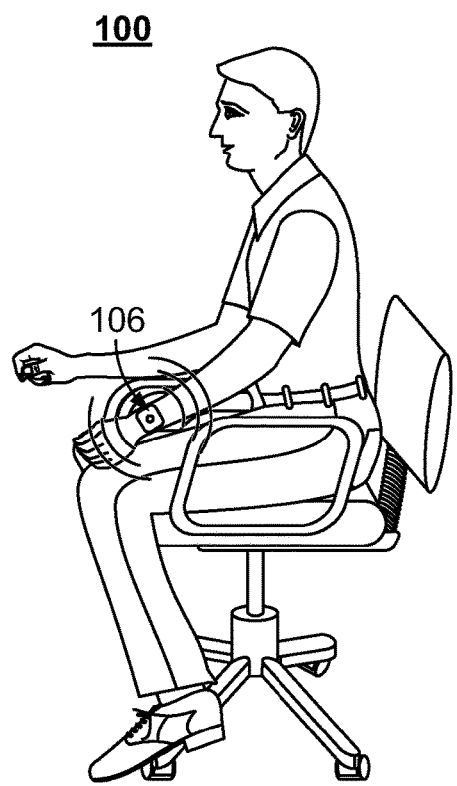

Systems and methods are described to address deficiencies in conventional biometric devices by dynamically enabling and disabling a biometric device based on the content the user is viewing. Suppose that a user is using a biometric device (e.g., Fitbit band) to track physical activity and vitals. For example, the Fitbit band may monitor the user's heart rate, sleeping patterns, steps taken, calories, etc. Rather than continuously collecting data, a media guidance application may be used to disable and enable data collection of the Fitbit band based on the content that the user is viewing. For example, the media guidance application may detect that the user is viewing a horror movie (e.g., "The Conjuring"), which features a scene presenting a jump scare. The scene may be associated with an enablement rule that causes the Fitbit band to begin tracking the user's heart rate. Once the scene starts, the Fitbit may start collecting heart rate measurements. Based on the user's reaction, the media guidance application may also provide a content recommendation. For example, if the user's heart rate did not change, it is possible that the user was not scared by the scene. Therefore, the media guidance application may recommend a scarier movie.

The amount of content available to users in any given content delivery system can be substantial. Consequently, many users desire a form of media guidance through an interface that allows users to efficiently navigate content selections and easily identify content that they may desire. An application that provides such guidance is referred to herein as an interactive media guidance application or, sometimes, a media guidance application or a guidance application.

Interactive media guidance applications may take various forms depending on the content for which they provide guidance. One typical type of media guidance application is an interactive television program guide. Interactive television program guides (sometimes referred to as electronic program guides) are well-known guidance applications that, among other things, allow users to navigate among and locate many types of content or media assets. Interactive media guidance applications may generate graphical user interface screens that enable a user to navigate among, locate and select content. As referred to herein, the terms "media asset" and "content" should be understood to mean an electronically consumable user asset, such as television programming, as well as pay-per-view programs, on-demand programs (as in video-on-demand (VOD) systems), Internet content (e.g., streaming content, downloadable content, Webcasts, etc.), video clips, audio, content information, pictures, rotating images, documents, playlists, websites, articles, books, electronic books, blogs, chat sessions, social media, applications, games, and/or any other media or multimedia and/or combination of the same. Guidance applications also allow users to navigate among and locate content. As referred to herein, the term "multimedia" should be understood to mean content that utilizes at least two different content forms described above, for example, text, audio, images, video, or interactivity content forms. Content may be recorded, played, displayed or accessed by user equipment devices, but can also be part of a live performance.

The media guidance application and/or any instructions for performing any of the embodiments discussed herein may be encoded on computer readable media. Computer readable media includes any media capable of storing data. The computer readable media may be transitory, including, but not limited to, propagating electrical or electromagnetic signals, or may be non-transitory including, but not limited to, volatile and non-volatile computer memory or storage devices such as a hard disk, floppy disk, USB drive, DVD, CD, media cards, register memory, processor caches, Random Access Memory ("RAM"), etc.

With the advent of the Internet, mobile computing, and high-speed wireless networks, users are accessing media on user equipment devices on which they traditionally did not. As referred to herein, the phrase "user equipment device," "user equipment," "user device," "electronic device," "electronic equipment," "media equipment device," or "media device" should be understood to mean any device for accessing the content described above, such as a television, a Smart TV, a set-top box, an integrated receiver decoder (IRD) for handling satellite television, a digital storage device, a digital media receiver (DMR), a digital media adapter (DMA), a streaming media device, a DVD player, a DVD recorder, a connected DVD, a local media server, a BLU-RAY player, a BLU-RAY recorder, a personal computer (PC), a laptop computer, a tablet computer, a WebTV box, a personal computer television (PC/TV), a PC media server, a PC media center, a hand-held computer, a stationary telephone, a personal digital assistant (PDA), a mobile telephone, a portable video player, a portable music player, a portable gaming machine, a smart phone, or any other television equipment, computing equipment, or wireless device, and/or combination of the same. In some embodiments, the user equipment device may have a front facing screen and a rear facing screen, multiple front screens, or multiple angled screens. In some embodiments, the user equipment device may have a front facing camera and/or a rear facing camera. On these user equipment devices, users may be able to navigate among and locate the same content available through a television. Consequently, media guidance may be available on these devices, as well. The guidance provided may be for content available only through a television, for content available only through one or more of other types of user equipment devices, or for content available both through a television and one or more of the other types of user equipment devices. The media guidance applications may be provided as on-line applications (i.e., provided on a web-site), or as stand-alone applications or clients on user equipment devices. Various devices and platforms that may implement media guidance applications are described in more detail below.

One of the functions of the media guidance application is to provide media guidance data to users. As referred to herein, the phrase "media guidance data" or "guidance data" should be understood to mean any data related to content or data used in operating the guidance application. For example, the guidance data may include program information, guidance application settings, user preferences, user profile information, media listings, media-related information (e.g., broadcast times, broadcast channels, titles, descriptions, ratings information (e.g., parental control ratings, critic's ratings, etc.), genre or category information, actor information, logo data for broadcasters' or providers' logos, etc.), media format (e.g., standard definition, high definition, 3D, etc.), on-demand information, blogs, websites, and any other type of guidance data that is helpful for a user to navigate among and locate desired content selections.

Figure 1B:
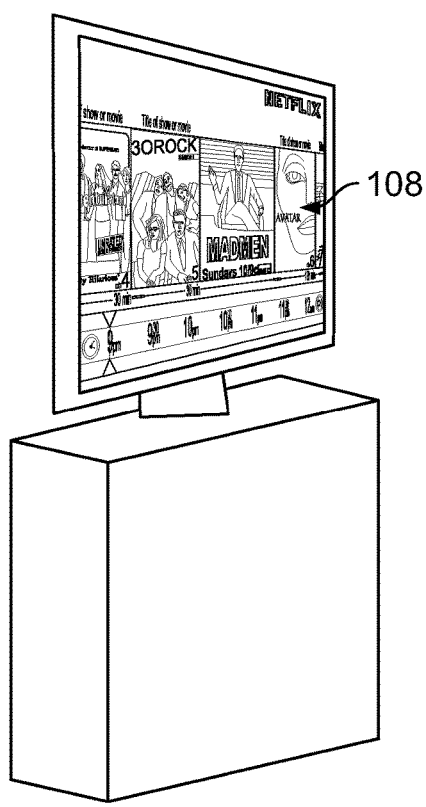
Figure 1B:
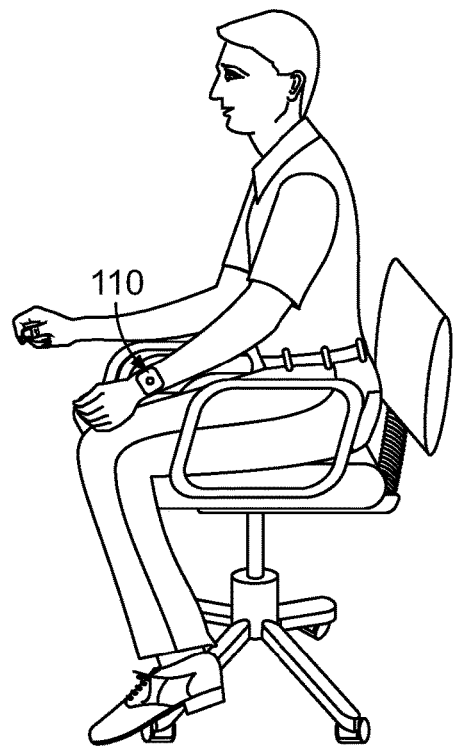

FIGS. 1A and 1B show illustrative examples of scenarios 100 and 106 for dynamically enabling and disabling a biometric device, in accordance with some embodiments of the disclosure. Suppose that the user is viewing the horror movie "Creature from the Black Lagoon," an on-demand media asset on display 102 (FIG. 1A). The media guidance application may retrieve a device enablement rule associated with the content. The media guidance application may retrieve metadata associated with the content being accessed. The metadata may include device enablement rules associated with the content. For example, the media guidance application may determine a device enablement rule that prompts biometric devices to collect heart rate measurements from the user.

The media guidance application may determine content criteria specified by the device enablement rule. A device enablement rule may be programmed with "if-else" logic. For example, the device enablement rule may be structured as "IF [Criteria 1] and/or [Criteria 2] . . . and/or [Criteria N], THEN [RESPONSE A1] and/or [RESPONSE A2] . . . and/or [RESPONSE AN]; ELSE [RESPONSE B1] and/or [RESPONSE B1] . . . and/or [RESPONSE BN]." In this structure, if a combination of the criteria, as established by the content provider or user, is met, the media guidance application will execute the respective response combination from the A set (e.g., A1, A2, etc.). If the combination of the criteria is not met, the media guidance application will execute the respective response combination from the B set (e.g., B1, B2, etc.). Suppose that the content provider established the device enablement rule states "IF the Creature appears in a scene, THEN enable the biometric device and prompt the biometric device to take a heart rate measurement; ELSE disable the biometric device." Suppose that the biometric device is the Fitbit band 106 (FIG. 1A). The content criteria in this device enablement rule is the appearance of the Creature, a character in "Creature from the Black Lagoon," in a scene of the movie.

It should be noted that the biometric device, represented in FIG. 1A as a Fitbit band, may be any device or smart technology that can monitor a characteristic of a user (e.g., facial expressions, movement, sounds, stress levels, eating habits, vitals, body temperature, etc.) Therefore, it is not necessary for the biometric device to be wearable, as depicted in FIG. 1A. The biometric device can be a sensor that monitors audio, video, motion, temperature, vitals, etc. For example, the biometric device may be an imaging device (e.g., Microsoft Kinect) which may track the user's expressions, pupil dilation, eye movements, etc. The biometric device may be a smart speaker (e.g., Google Home, Amazon Echo, etc.) that may monitor sounds made by the user, such as talking, laughing, crying, etc.

The media guidance application may retrieve metadata associated with the content being accessed on the user equipment that matches the content criteria. The media guidance application may refer to the metadata associated with the movie to determine the characters that appear in the movie at various playback positions (e.g., the Creature). The device enablement rule may also specify the playback positions in which the Creature appears in the movie. For example, the device enablement rule may state "IF playback is at position 0:12:57 or 0:50:12 or 1:24:23, THEN enable the biometric device and prompt the biometric device to take a heart rate measurement; ELSE disable the biometric device." The content criteria in this case points to specific playback positions in the movie, such as 12 minutes and 57 seconds from the start (e.g., 0:12:57). Once playback to the user reaches this point, the content criteria may be satisfied.

It should be noted that the device enablement rule may enable multiple biometric devices and may chain commands. For example, a device enablement rule may state "IF playback is at position 0:12:57, THEN enable the first biometric device to take a heart rate measurement (AND IF the heart rate measurement exceeds 100 beats per minute, enable a second biometric device to collect audio samples; ELSE disable the second biometric device) ELSE disable the first biometric device." In this case, the first biometric device may be a heart monitor and the second biometric device may be a smart speaker, a mobile phone, an audio recorder, etc. The media guidance application may determine whether the first condition is met, and in response to determining that the first condition is met, may execute the condition in the parentheses. In another example, the device enablement rule may state "IF playback is at scene two, THEN enable the first biometric device to take a heart rate measurement and enable the second biometric device to assess body heat; ELSE disable the first biometric device and the second biometric device." In this case, the first biometric device may be a light sensor that approximates heart rate, and the second biometric device may be a heat gun or an infrared sensor that can collect the user's heat signature. The biometric devices mentioned above may be wearable, or may be placed far away from the user.

The media guidance application may compare the retrieved metadata to a condition specified by the device enablement rule, to determine whether the content being accessed on the user equipment satisfies the device enablement rule. For example, if the user is on playback position 0:12:57, the media guidance application may determine that the content criteria of the device enablement rule is satisfied. Screen content 104 displays the Creature on the screen.

The media guidance application may temporarily activate the identified biometric device while the content being accessed continues to satisfy the device enablement rule. Returning to the overarching example, the media guidance application may identify that the user is wearing his/her Fitbit band (e.g., biometric device 106). In addition, the media guidance application may determine that the Creature has appeared in a scene being viewed by the user. In response, the media guidance application may determine that the content criteria of the device enablement rule have been satisfied, and may enable the biometric device. For example, the media guidance application may utilize IR (infrared radiation) signals to activate the biometric device. The media guidance application may use the Internet to communicate with and activate the biometric device. The media guidance application may also prompt the user to manually activate the biometric device. Furthermore, the user's Fitbit may remain enabled (e.g., as depicted with signals emanating from biometric device 106) until the Creature exits the scene.

The media guidance application may measure a biometric response of the user to the content being accessed while the biometric device is activated. For example, while the Creature is in the scene being viewed by the user, the media guidance application may ensure that the user's Fitbit band is active and is collecting the user's heart rate.

The media guidance application may then generate a content recommendation based on the measured biometric response, as shown in screen content 108 (FIG. 1B), which is a display of content that may be of interest to the user. Suppose that in a certain scene, the Creature appears. Metadata associated with the device enablement rule may indicate that the expected biometric response should be in a heart rate range of 90-100 beats per minute. The media guidance application may refer to a biometrics database that includes information about different levels of biometric responses. As previously mentioned, the biometrics database may have a heart rate table classifying various heart rate levels. For example, 80-100 beats per minute may be classified as an accelerated heart rate and 100-120 may be classified as very accelerated, in the heart rate table. Based on the heart rate table, the media guidance application may therefore determine that the user's heart rate is in the "very accelerated" heart rate class and is not in the expected "accelerated" class, as indicated in the expected biometric response. In response, the content recommendations depicted in screen content 108 may include media assets with a lower heart rate class (e.g., slightly-accelerated). It should also be noted that because the Creature is no longer on the screen, the media guidance application has deactivated (also interchangeably used with "disabled") biometric device 110 (FIG. 1B). As a result, the user's heart rate is no longer being measured in FIG. 1B. Deactivating the device may simply involve stopping the device from collecting data until further instruction from the user or media guidance application. In some cases, deactivating may involve sending the biometric device into sleep mode, a lower power mode, or completely shutting the power down. Just as previously mentioned, the media guidance application may communicate with the biometric device using IR signals, over the Internet, or through prompts to the user for manually activating or deactivating. Communications between the media guidance application and the biometric device may be performed over communication network 514 (e.g., discussed in description of FIG. 5).

Figure 2:
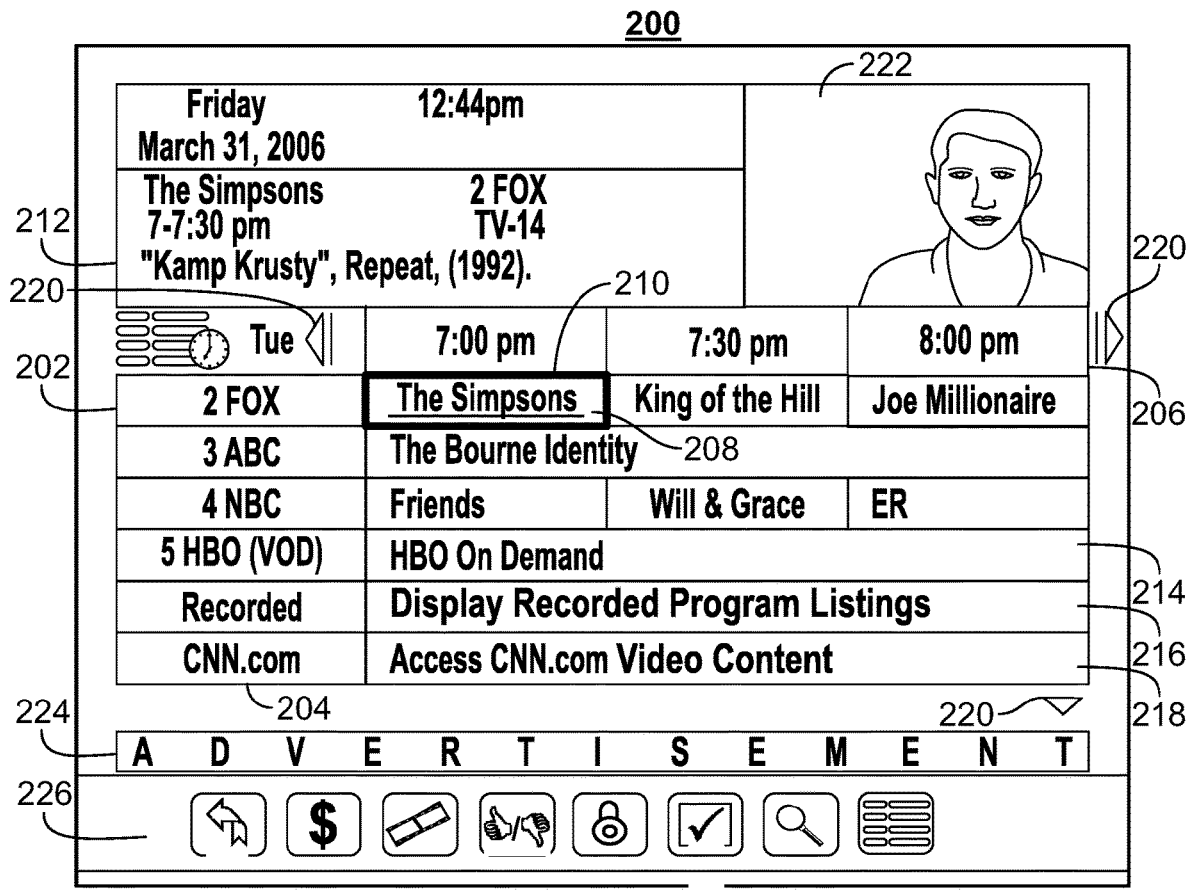
FIGS. 2 and 3 show illustrative examples of display screens generated by a media guidance application in accordance with some embodiments of the disclosure.
Figure 3:
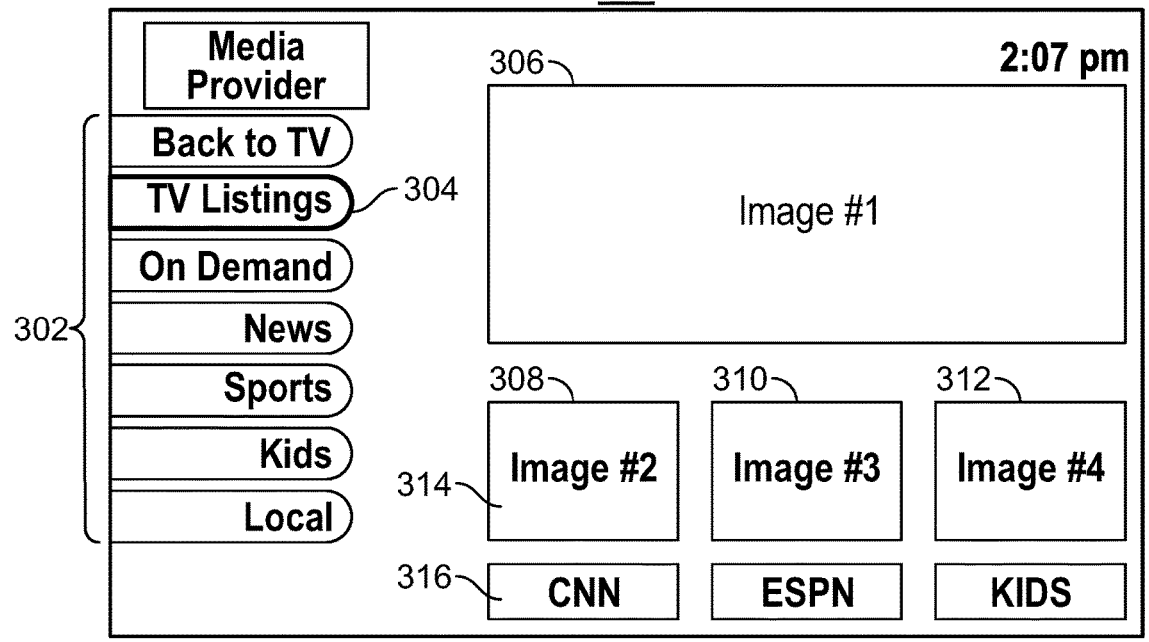

FIGS. 2-3 show illustrative display screens that may be used to provide media guidance data. The display screens shown in FIGS. 2-3 may be implemented on any suitable user equipment device or platform. While the displays of FIGS. 2-3 are illustrated as full screen displays, they may also be fully or partially overlaid over content being displayed. A user may indicate a desire to access content information by selecting a selectable option provided in a display screen (e.g., a menu option, a listings option, an icon, a hyperlink, etc.) or pressing a dedicated button (e.g., a GUIDE button) on a remote control or other user input interface or device. In response to the user's indication, the media guidance application may provide a display screen with media guidance data organized in one of several ways, such as by time and channel in a grid, by time, by channel, by source, by content type, by category (e.g., movies, sports, news, children, or other categories of programming), or other predefined, user-defined, or other organization criteria.

FIG. 2 shows illustrative grid of a program listings display 200 arranged by time and channel that also enables access to different types of content in a single display. Display 200 may include grid 202 with: (1) a column of channel/content type identifiers 204, where each channel/content type identifier (which is a cell in the column) identifies a different channel or content type available; and (2) a row of time identifiers 206, where each time identifier (which is a cell in the row) identifies a time block of programming. Grid 202 also includes cells of program listings, such as program listing 208, where each listing provides the title of the program provided on the listing's associated channel and time. With a user input device, a user can select program listings by moving highlight region 210. Information relating to the program listing selected by highlight region 210 may be provided in program information region 212. Region 212 may include, for example, the program title, the program description, the time the program is provided (if applicable), the channel the program is on (if applicable), the program's rating, and other desired information.

In addition to providing access to linear programming (e.g., content that is scheduled to be transmitted to a plurality of user equipment devices at a predetermined time and is provided according to a schedule), the media guidance application also provides access to non-linear programming (e.g., content accessible to a user equipment device at any time and is not provided according to a schedule). Non-linear programming may include content from different content sources including on-demand content (e.g., VOD), Internet content (e.g., streaming media, downloadable media, etc.), locally stored content (e.g., content stored on any user equipment device described above or other storage device), or other time-independent content. On-demand content may include movies or any other content provided by a particular content provider (e.g., HBO On Demand providing "The Sopranos" and "Curb Your Enthusiasm"). HBO ON DEMAND is a service mark owned by Time Warner Company L.P. et al. and THE SOPRANOS and CURB YOUR ENTHUSIASM are trademarks owned by the Home Box Office, Inc. Internet content may include web events, such as a chat session or Webcast, or content available on-demand as streaming content or downloadable content through an Internet web site or other Internet access (e.g. FTP).

Grid 202 may provide media guidance data for non-linear programming including on-demand listing 214, recorded content listing 216, and Internet content listing 218. A display combining media guidance data for content from different types of content sources is sometimes referred to as a "mixed-media" display. Various permutations of the types of media guidance data that may be displayed that are different than display 200 may be based on user selection or guidance application definition (e.g., a display of only recorded and broadcast listings, only on-demand and broadcast listings, etc.). As illustrated, listings 214, 216, and 218 are shown as spanning the entire time block displayed in grid 202 to indicate that selection of these listings may provide access to a display dedicated to on-demand listings, recorded listings, or Internet listings, respectively. In some embodiments, listings for these content types may be included directly in grid 202. Additional media guidance data may be displayed in response to the user selecting one of the navigational icons 220. (Pressing an arrow key on a user input device may affect the display in a similar manner as selecting navigational icons 220.)

Display 200 may also include video region 222, and options region 226. Video region 222 may allow the user to view and/or preview programs that are currently available, will be available, or were available to the user. The content of video region 222 may correspond to, or be independent from, one of the listings displayed in grid 202. Grid displays including a video region are sometimes referred to as picture-in-guide (PIG) displays. PIG displays and their functionalities are described in greater detail in Satterfield et al. U.S. Pat. No. 6,564,378, issued May 13, 2003 and Yuen et al. U.S. Pat. No. 6,239,794, issued May 29, 2001, which are hereby incorporated by reference herein in their entireties. PIG displays may be included in other media guidance application display screens of the embodiments described herein.

Options region 226 may allow the user to access different types of content, media guidance application displays, and/or media guidance application features. Options region 226 may be part of display 200 (and other display screens described herein), or may be invoked by a user by selecting an on-screen option or pressing a dedicated or assignable button on a user input device. The selectable options within options region 226 may concern features related to program listings in grid 202 or may include options available from a main menu display. Features related to program listings may include searching for other air times or ways of receiving a program, recording a program, enabling series recording of a program, setting program and/or channel as a favorite, purchasing a program, or other features. Options available from a main menu display may include search options, VOD options, parental control options, Internet options, cloud-based options, device synchronization options, second screen device options, options to access various types of media guidance data displays, options to subscribe to a premium service, options to edit a user's profile, options to access a browse overlay, or other options.

The media guidance application may be personalized based on a user's preferences. A personalized media guidance application allows a user to customize displays and features to create a personalized "experience" with the media guidance application. This personalized experience may be created by allowing a user to input these customizations and/or by the media guidance application monitoring user activity to determine various user preferences. Users may access their personalized guidance application by logging in or otherwise identifying themselves to the guidance application. Customization of the media guidance application may be made in accordance with a user profile. The customizations may include varying presentation schemes (e.g., color scheme of displays, font size of text, etc.), aspects of content listings displayed (e.g., only HDTV or only 3D programming, user-specified broadcast channels based on favorite channel selections, re-ordering the display of channels, recommended content, etc.), desired recording features (e.g., recording or series recordings for particular users, recording quality, etc.), parental control settings, customized presentation of Internet content (e.g., presentation of social media content, e-mail, electronically delivered articles, etc.) and other desired customizations.

The media guidance application may allow a user to provide user profile information or may automatically compile user profile information. The media guidance application may, for example, monitor the content the user accesses and/or other interactions the user may have with the guidance application. Additionally, the media guidance application may obtain all or part of other user profiles that are related to a particular user (e.g., from other web sites on the Internet the user accesses, such as www.Tivo.com, from other media guidance applications the user accesses, from other interactive applications the user accesses, from another user equipment device of the user, etc.), and/or obtain information about the user from other sources that the media guidance application may access. As a result, a user can be provided with a unified guidance application experience across the user's different user equipment devices. This type of user experience is described in greater detail below in connection with FIG. 5. Additional personalized media guidance application features are described in greater detail in Ellis et al., U.S. Patent Application Publication No. 2005/0251827, filed Jul. 11, 2005, Boyer et al., U.S. Pat. No. 7,165,098, issued Jan. 16, 2007, and Ellis et al., U.S. Patent Application Publication No. 2002/0174430, filed Feb. 21, 2002, which are hereby incorporated by reference herein in their entireties.

Another display arrangement for providing media guidance is shown in FIG. 3. Video mosaic display 300 includes selectable options 302 for content information organized based on content type, genre, and/or other organization criteria. In display 300, television listings option 304 is selected, thus providing listings 306, 308, 310, and 312 as broadcast program listings. In display 300 the listings may provide graphical images including cover art, still images from the content, video clip previews, live video from the content, or other types of content that indicate to a user the content being described by the media guidance data in the listing. Each of the graphical listings may also be accompanied by text to provide further information about the content associated with the listing. For example, listing 308 may include more than one portion, including media portion 314 and text portion 316. Media portion 314 and/or text portion 316 may be selectable to view content in full-screen or to view information related to the content displayed in media portion 314 (e.g., to view listings for the channel that the video is displayed on).

The listings in display 300 are of different sizes (i.e., listing 306 is larger than listings 308, 310, and 312), but if desired, all the listings may be the same size. Listings may be of different sizes or graphically accentuated to indicate degrees of interest to the user or to emphasize certain content, as desired by the content provider or based on user preferences. Various systems and methods for graphically accentuating content listings are discussed in, for example, Yates, U.S. Patent Application Publication No. 2010/0153885, filed Nov. 12, 2009, which is hereby incorporated by reference herein in its entirety.

Figure 4:
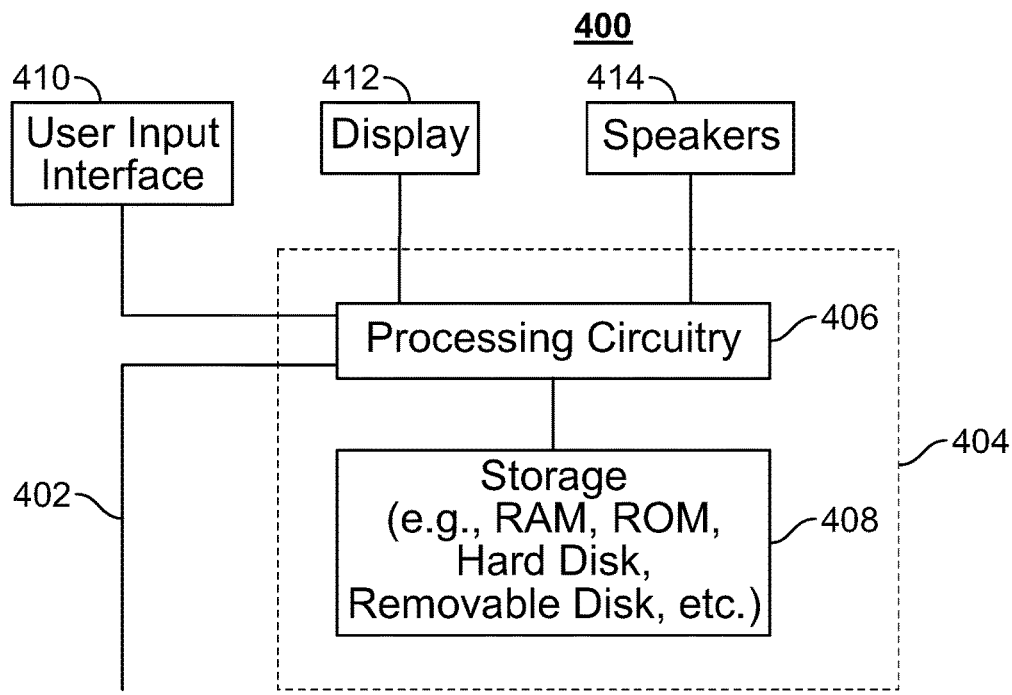
FIG. 4 is a block diagram of an illustrative user equipment device in accordance with some embodiments of the disclosure.

Users may access content and the media guidance application (and its display screens described above and below) from one or more of their user equipment devices. FIG. 4 shows a generalized embodiment of illustrative user equipment device 400. More specific implementations of user equipment devices are discussed below in connection with FIG. 5. User equipment device 400 may receive content and data via input/output (hereinafter "I/O") path 402. I/O path 402 may provide content (e.g., broadcast programming, on-demand programming, Internet content, content available over a local area network (LAN) or wide area network (WAN), and/or other content) and data to control circuitry 404, which includes processing circuitry 406 and storage 408. Control circuitry 404 may be used to send and receive commands, requests, and other suitable data using I/O path 402. I/O path 402 may connect control circuitry 404 (and specifically processing circuitry 406) to one or more communications paths (described below). I/O functions may be provided by one or more of these communications paths, but are shown as a single path in FIG. 4 to avoid overcomplicating the drawing.

Control circuitry 404 may be based on any suitable processing circuitry such as processing circuitry 406. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, processing circuitry may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, control circuitry 404 executes instructions for a media guidance application stored in memory (i.e., storage 408). Specifically, control circuitry 404 may be instructed by the media guidance application to perform the functions discussed above and below. For example, the media guidance application may provide instructions to control circuitry 404 to generate the media guidance displays. In some implementations, any action performed by control circuitry 404 may be based on instructions received from the media guidance application.

In client-server based embodiments, control circuitry 404 may include communications circuitry suitable for communicating with a guidance application server or other networks or servers. The instructions for carrying out the above-mentioned functionality may be stored on the guidance application server. Communications circuitry may include a cable modem, an integrated services digital network (ISDN) modem, a digital subscriber line (DSL) modem, a telephone modem, Ethernet card, or a wireless modem for communications with other equipment, or any other suitable communications circuitry. Such communications may involve the Internet or any other suitable communications networks or paths (which is described in more detail in connection with FIG. 5). In addition, communications circuitry may include circuitry that enables peer-to-peer communication of user equipment devices, or communication of user equipment devices in locations remote from each other (described in more detail below).

Memory may be an electronic storage device provided as storage 408 that is part of control circuitry 404. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVR, sometimes called a personal video recorder, or PVR), solid state devices, quantum storage devices, gaming consoles, gaming media, or any other suitable fixed or removable storage devices, and/or any combination of the same. Storage 408 may be used to store various types of content described herein as well as media guidance data described above. Nonvolatile memory may also be used (e.g., to launch a boot-up routine and other instructions). Cloud-based storage, described in relation to FIG. 5, may be used to supplement storage 408 or instead of storage 408.

Control circuitry 404 may include video generating circuitry and tuning circuitry, such as one or more analog tuners, one or more MPEG-2 decoders or other digital decoding circuitry, high-definition tuners, or any other suitable tuning or video circuits or combinations of such circuits. Encoding circuitry (e.g., for converting over-the-air, analog, or digital signals to MPEG signals for storage) may also be provided. Control circuitry 404 may also include scaler circuitry for upconverting and downconverting content into the preferred output format of the user equipment 400. Circuitry 404 may also include digital-to-analog converter circuitry and analog-to-digital converter circuitry for converting between digital and analog signals. The tuning and encoding circuitry may be used by the user equipment device to receive and to display, to play, or to record content. The tuning and encoding circuitry may also be used to receive guidance data. The circuitry described herein, including for example, the tuning, video generating, encoding, decoding, encrypting, decrypting, scaler, and analog/digital circuitry, may be implemented using software running on one or more general purpose or specialized processors. Multiple tuners may be provided to handle simultaneous tuning functions (e.g., watch and record functions, picture-in-picture (PIP) functions, multiple-tuner recording, etc.). If storage 408 is provided as a separate device from user equipment 400, the tuning and encoding circuitry (including multiple tuners) may be associated with storage 408.

A user may send instructions to control circuitry 404 using user input interface 410. User input interface 410 may be any suitable user interface, such as a remote control, mouse, trackball, keypad, keyboard, touch screen, touchpad, stylus input, joystick, voice recognition interface, or other user input interfaces. Display 412 may be provided as a stand-alone device or integrated with other elements of user equipment device 400. For example, display 412 may be a touchscreen or touch-sensitive display. In such circumstances, user input interface 410 may be integrated with or combined with display 412. Display 412 may be one or more of a monitor, a television, a liquid crystal display (LCD) for a mobile device, amorphous silicon display, low temperature poly silicon display, electronic ink display, electrophoretic display, active matrix display, electro-wetting display, electrofluidic display, cathode ray tube display, light-emitting diode display, electroluminescent display, plasma display panel, high-performance addressing display, thin-film transistor display, organic light-emitting diode display, surface-conduction electron-emitter display (SED), laser television, carbon nanotubes, quantum dot display, interferometric modulator display, or any other suitable equipment for displaying visual images. In some embodiments, display 412 may be HDTV-capable. In some embodiments, display 412 may be a 3D display, and the interactive media guidance application and any suitable content may be displayed in 3D. A video card or graphics card may generate the output to the display 412. The video card may offer various functions such as accelerated rendering of 3D scenes and 2D graphics, MPEG-2/MPEG-4 decoding, TV output, or the ability to connect multiple monitors. The video card may be any processing circuitry described above in relation to control circuitry 404. The video card may be integrated with the control circuitry 404. Speakers 414 may be provided as integrated with other elements of user equipment device 400 or may be stand-alone units. The audio component of videos and other content displayed on display 412 may be played through speakers 414. In some embodiments, the audio may be distributed to a receiver (not shown), which processes and outputs the audio via speakers 414.

The guidance application may be implemented using any suitable architecture. For example, it may be a stand-alone application wholly-implemented on user equipment device 400. In such an approach, instructions of the application are stored locally (e.g., in storage 408), and data for use by the application is downloaded on a periodic basis (e.g., from an out-of-band feed, from an Internet resource, or using another suitable approach). Control circuitry 404 may retrieve instructions of the application from storage 408 and process the instructions to generate any of the displays discussed herein. Based on the processed instructions, control circuitry 404 may determine what action to perform when input is received from input interface 410. For example, movement of a cursor on a display up/down may be indicated by the processed instructions when input interface 410 indicates that an up/down button was selected.

In some embodiments, the media guidance application is a client-server based application. Data for use by a thick or thin client implemented on user equipment device 400 is retrieved on-demand by issuing requests to a server remote to the user equipment device 400. In one example of a client-server based guidance application, control circuitry 404 runs a web browser that interprets web pages provided by a remote server. For example, the remote server may store the instructions for the application in a storage device. The remote server may process the stored instructions using circuitry (e.g., control circuitry 404) and generate the displays discussed above and below. The client device may receive the displays generated by the remote server and may display the content of the displays locally on equipment device 400. This way, the processing of the instructions is performed remotely by the server while the resulting displays are provided locally on equipment device 400. Equipment device 400 may receive inputs from the user via input interface 410 and transmit those inputs to the remote server for processing and generating the corresponding displays. For example, equipment device 400 may transmit a communication to the remote server indicating that an up/down button was selected via input interface 410. The remote server may process instructions in accordance with that input and generate a display of the application corresponding to the input (e.g., a display that moves a cursor up/down). The generated display is then transmitted to equipment device 400 for presentation to the user.

In some embodiments, the media guidance application is downloaded and interpreted or otherwise run by an interpreter or virtual machine (run by control circuitry 404). In some embodiments, the guidance application may be encoded in the ETV Binary Interchange Format (EBIF), received by control circuitry 404 as part of a suitable feed, and interpreted by a user agent running on control circuitry 404. For example, the guidance application may be an EBIF application. In some embodiments, the guidance application may be defined by a series of JAVA-based files that are received and run by a local virtual machine or other suitable middleware executed by control circuitry 404. In some of such embodiments (e.g., those employing MPEG-2 or other digital media encoding schemes), the guidance application may be, for example, encoded and transmitted in an MPEG-2 object carousel with the MPEG audio and video packets of a program.

Figure 5:
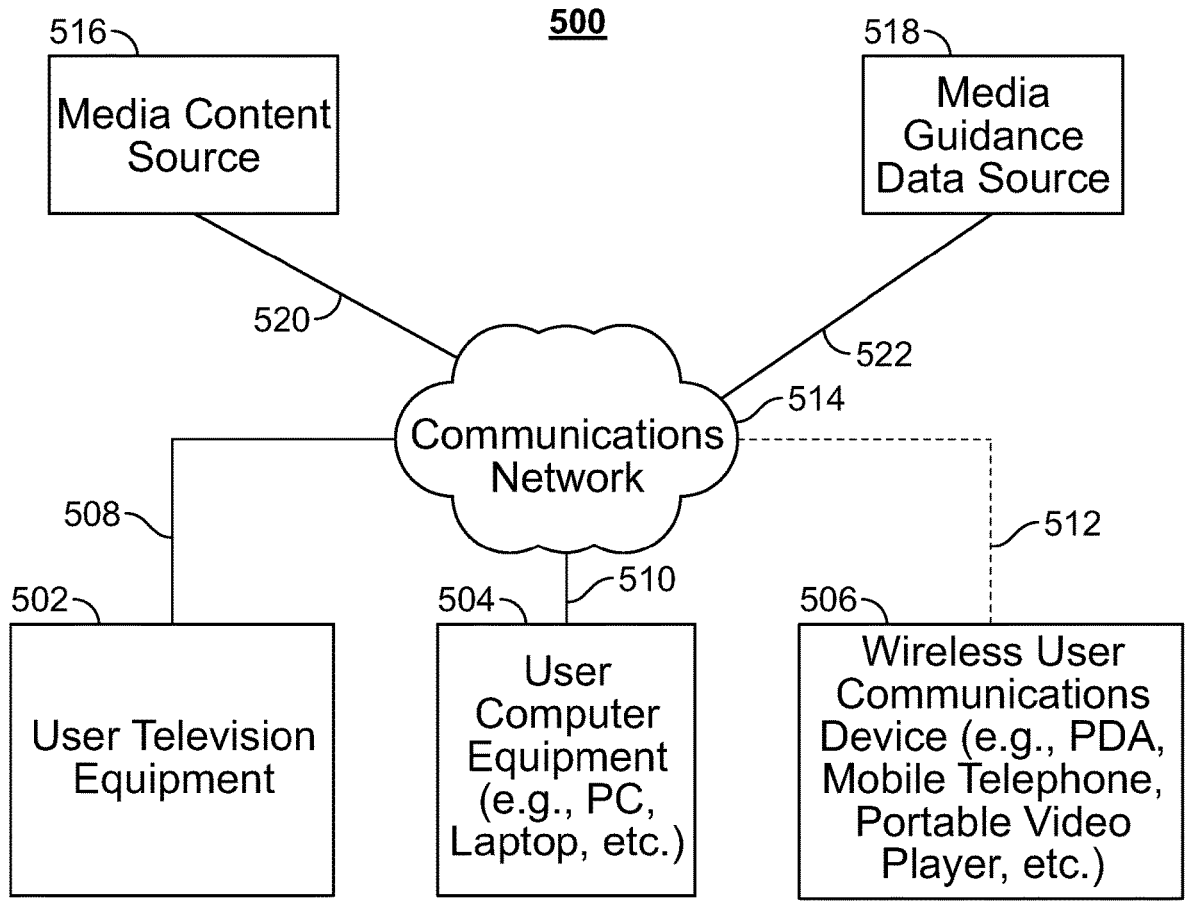
FIG. 5 is a block diagram of an illustrative media system in accordance with some embodiments of the disclosure.

User equipment device 400 of FIG. 4 can be implemented in system 500 of FIG. 5 as user television equipment 502, user computer equipment 504, wireless user communications device 506, or any other type of user equipment suitable for accessing content, such as a non-portable gaming machine. For simplicity, these devices may be referred to herein collectively as user equipment or user equipment devices, and may be substantially similar to user equipment devices described above. User equipment devices, on which a media guidance application may be implemented, may function as a standalone device or may be part of a network of devices. Various network configurations of devices may be implemented and are discussed in more detail below.

A user equipment device utilizing at least some of the system features described above in connection with FIG. 4 may not be classified solely as user television equipment 502, user computer equipment 504, or a wireless user communications device 506. For example, user television equipment 502 may, like some user computer equipment 504, be Internet-enabled allowing for access to Internet content, while user computer equipment 504 may, like some television equipment 502, include a tuner allowing for access to television programming. The media guidance application may have the same layout on various different types of user equipment or may be tailored to the display capabilities of the user equipment. For example, on user computer equipment 504, the guidance application may be provided as a web site accessed by a web browser. In another example, the guidance application may be scaled down for wireless user communications devices 506.

In system 500, there is typically more than one of each type of user equipment device but only one of each is shown in FIG. 5 to avoid overcomplicating the drawing. In addition, each user may utilize more than one type of user equipment device and also more than one of each type of user equipment device.

In some embodiments, a user equipment device (e.g., user television equipment 502, user computer equipment 504, wireless user communications device 506) may be referred to as a "second screen device." For example, a second screen device may supplement content presented on a first user equipment device. The content presented on the second screen device may be any suitable content that supplements the content presented on the first device. In some embodiments, the second screen device provides an interface for adjusting settings and display preferences of the first device. In some embodiments, the second screen device is configured for interacting with other second screen devices or for interacting with a social network. The second screen device can be located in the same room as the first device, a different room from the first device but in the same house or building, or in a different building from the first device.

The user may also set various settings to maintain consistent media guidance application settings across in-home devices and remote devices. Settings include those described herein, as well as channel and program favorites, programming preferences that the guidance application utilizes to make programming recommendations, display preferences, and other desirable guidance settings. For example, if a user sets a channel as a favorite on, for example, the web site www.Tivo.com on their personal computer at their office, the same channel would appear as a favorite on the user's in-home devices (e.g., user television equipment and user computer equipment) as well as the user's mobile devices, if desired. Therefore, changes made on one user equipment device can change the guidance experience on another user equipment device, regardless of whether they are the same or a different type of user equipment device. In addition, the changes made may be based on settings input by a user, as well as user activity monitored by the guidance application.

The user equipment devices may be coupled to communications network 514. Namely, user television equipment 502, user computer equipment 504, and wireless user communications device 506 are coupled to communications network 514 via communications paths 508, 510, and 512, respectively. Communications network 514 may be one or more networks including the Internet, a mobile phone network, mobile voice or data network (e.g., a 4G or LTE network), cable network, public switched telephone network, or other types of communications network or combinations of communications networks. Paths 508, 510, and 512 may separately or together include one or more communications paths, such as, a satellite path, a fiber-optic path, a cable path, a path that supports Internet communications (e.g., IPTV), free-space connections (e.g., for broadcast or other wireless signals), or any other suitable wired or wireless communications path or combination of such paths. Path 512 is drawn with dotted lines to indicate that in the exemplary embodiment shown in FIG. 5 it is a wireless path and paths 508 and 510 are drawn as solid lines to indicate they are wired paths (although these paths may be wireless paths, if desired). Communications with the user equipment devices may be provided by one or more of these communications paths, but are shown as a single path in FIG. 5 to avoid overcomplicating the drawing.

Although communications paths are not drawn between user equipment devices, these devices may communicate directly with each other via communication paths, such as those described above in connection with paths 508, 510, and 512, as well as other short-range point-to-point communication paths, such as USB cables, IEEE 1394 cables, wireless paths (e.g., Bluetooth, infrared, IEEE 802-11x, etc.), or other short-range communication via wired or wireless paths. BLUETOOTH is a certification mark owned by Bluetooth SIG, INC. The user equipment devices may also communicate with each other directly through an indirect path via communications network 514.

System 500 includes content source 516 and media guidance data source 518 coupled to communications network 514 via communication paths 520 and 522, respectively. Paths 520 and 522 may include any of the communication paths described above in connection with paths 508, 510, and 512. Communications with the content source 516 and media guidance data source 518 may be exchanged over one or more communications paths, but are shown as a single path in FIG. 5 to avoid overcomplicating the drawing. In addition, there may be more than one of each of content source 516 and media guidance data source 518, but only one of each is shown in FIG. 5 to avoid overcomplicating the drawing. (The different types of each of these sources are discussed below.) If desired, content source 516 and media guidance data source 518 may be integrated as one source device. Although communications between sources 516 and 518 with user equipment devices 502, 504, and 506 are shown as through communications network 514, in some embodiments, sources 516 and 518 may communicate directly with user equipment devices 502, 504, and 506 via communication paths (not shown) such as those described above in connection with paths 508, 510, and 512.

Content source 516 may include one or more types of content distribution equipment including a television distribution facility, cable system headend, satellite distribution facility, programming sources (e.g., television broadcasters, such as NBC, ABC, HBO, etc.), intermediate distribution facilities and/or servers, Internet providers, on-demand media servers, and other content providers. NBC is a trademark owned by the National Broadcasting Company, Inc., ABC is a trademark owned by the American Broadcasting Company, Inc., and HBO is a trademark owned by the Home Box Office, Inc. Content source 516 may be the originator of content (e.g., a television broadcaster, a Webcast provider, etc.) or may not be the originator of content (e.g., an on-demand content provider, an Internet provider of content of broadcast programs for downloading, etc.). Content source 516 may include cable sources, satellite providers, on-demand providers, Internet providers, over-the-top content providers, or other providers of content. Content source 516 may also include a remote media server used to store different types of content (including video content selected by a user), in a location remote from any of the user equipment devices. Systems and methods for remote storage of content, and providing remotely stored content to user equipment are discussed in greater detail in connection with Ellis et al., U.S. Pat. No. 7,761,892, issued Jul. 20, 2010, which is hereby incorporated by reference herein in its entirety.

Media guidance data source 518 may provide media guidance data, such as the media guidance data described above. Media guidance data may be provided to the user equipment devices using any suitable approach. In some embodiments, the guidance application may be a standalone interactive television program guide that receives program guide data via a data feed (e.g., a continuous feed or trickle feed). Program schedule data and other guidance data may be provided to the user equipment on a television channel sideband, using an in-band digital signal, using an out-of-band digital signal, or by any other suitable data transmission technique. Program schedule data and other media guidance data may be provided to user equipment on multiple analog or digital television channels.

In some embodiments, guidance data from media guidance data source 518 may be provided to users' equipment using a client-server approach. For example, a user equipment device may pull media guidance data from a server, or a server may push media guidance data to a user equipment device. In some embodiments, a guidance application client residing on the user's equipment may initiate sessions with source 518 to obtain guidance data when needed, e.g., when the guidance data is out of date or when the user equipment device receives a request from the user to receive data. Media guidance may be provided to the user equipment with any suitable frequency (e.g., continuously, daily, a user-specified period of time, a system-specified period of time, in response to a request from user equipment, etc.). Media guidance data source 518 may provide user equipment devices 502, 504, and 506 the media guidance application itself or software updates for the media guidance application.

In some embodiments, the media guidance data may include viewer data. For example, the viewer data may include current and/or historical user activity information (e.g., what content the user typically watches, what times of day the user watches content, whether the user interacts with a social network, at what times the user interacts with a social network to post information, what types of content the user typically watches (e.g., pay TV or free TV), mood, brain activity information, etc.). The media guidance data may also include subscription data. For example, the subscription data may identify to which sources or services a given user subscribes and/or to which sources or services the given user has previously subscribed but later terminated access (e.g., whether the user subscribes to premium channels, whether the user has added a premium level of services, whether the user has increased Internet speed). In some embodiments, the viewer data and/or the subscription data may identify patterns of a given user for a period of more than one year. The media guidance data may include a model (e.g., a survivor model) used for generating a score that indicates a likelihood a given user will terminate access to a service/source. For example, the media guidance application may process the viewer data with the subscription data using the model to generate a value or score that indicates a likelihood of whether the given user will terminate access to a particular service or source. In particular, a higher score may indicate a higher level of confidence that the user will terminate access to a particular service or source. Based on the score, the media guidance application may generate promotions that entice the user to keep the particular service or source indicated by the score as one to which the user will likely terminate access.

Media guidance applications may be, for example, standalone applications implemented on user equipment devices. For example, the media guidance application may be implemented as software or a set of executable instructions which may be stored in storage 408, and executed by control circuitry 404 of a user equipment device 400. In some embodiments, media guidance applications may be client-server applications where only a client application resides on the user equipment device, and server application resides on a remote server. For example, media guidance applications may be implemented partially as a client application on control circuitry 404 of user equipment device 400 and partially on a remote server as a server application (e.g., media guidance data source 518) running on control circuitry of the remote server. When executed by control circuitry of the remote server (such as media guidance data source 518), the media guidance application may instruct the control circuitry to generate the guidance application displays and transmit the generated displays to the user equipment devices. The server application may instruct the control circuitry of the media guidance data source 518 to transmit data for storage on the user equipment. The client application may instruct control circuitry of the receiving user equipment to generate the guidance application displays.

Content and/or media guidance data delivered to user equipment devices 502, 504, and 506 may be over-the-top (OTT) content. OTT content delivery allows Internet-enabled user devices, including any user equipment device described above, to receive content that is transferred over the Internet, including any content described above, in addition to content received over cable or satellite connections. OTT content is delivered via an Internet connection provided by an Internet service provider (ISP), but a third party distributes the content. The ISP may not be responsible for the viewing abilities, copyrights, or redistribution of the content, and may only transfer IP packets provided by the OTT content provider. Examples of OTT content providers include YOUTUBE, NETFLIX, and HULU, which provide audio and video via IP packets. Youtube is a trademark owned by Google Inc., Netflix is a trademark owned by Netflix Inc., and Hulu is a trademark owned by Hulu, LLC. OTT content providers may additionally or alternatively provide media guidance data described above. In addition to content and/or media guidance data, providers of OTT content can distribute media guidance applications (e.g., web-based applications or cloud-based applications), or the content can be displayed by media guidance applications stored on the user equipment device.

Media guidance system 500 is intended to illustrate a number of approaches, or network configurations, by which user equipment devices and sources of content and guidance data may communicate with each other for the purpose of accessing content and providing media guidance. The embodiments described herein may be applied in any one or a subset of these approaches, or in a system employing other approaches for delivering content and providing media guidance. The following four approaches provide specific illustrations of the generalized example of FIG. 5.

In one approach, user equipment devices may communicate with each other within a home network. User equipment devices can communicate with each other directly via short-range point-to-point communication schemes described above, via indirect paths through a hub or other similar device provided on a home network, or via communications network 514. Each of the multiple individuals in a single home may operate different user equipment devices on the home network. As a result, it may be desirable for various media guidance information or settings to be communicated between the different user equipment devices. For example, it may be desirable for users to maintain consistent media guidance application settings on different user equipment devices within a home network, as described in greater detail in Ellis et al., U.S. Patent Publication No. 2005/0251827, filed Jul. 11, 2005. Different types of user equipment devices in a home network may also communicate with each other to transmit content. For example, a user may transmit content from user computer equipment to a portable video player or portable music player.

In a second approach, users may have multiple types of user equipment by which they access content and obtain media guidance. For example, some users may have home networks that are accessed by in-home and mobile devices. Users may control in-home devices via a media guidance application implemented on a remote device. For example, users may access an online media guidance application on a website via a personal computer at their office, or a mobile device such as a PDA or web-enabled mobile telephone. The user may set various settings (e.g., recordings, reminders, or other settings) on the online guidance application to control the user's in-home equipment. The online guide may control the user's equipment directly, or by communicating with a media guidance application on the user's in-home equipment. Various systems and methods for user equipment devices communicating, where the user equipment devices are in locations remote from each other, is discussed in, for example, Ellis et al., U.S. Pat. No. 8,046,801, issued Oct. 25, 2011, which is hereby incorporated by reference herein in its entirety.

In a third approach, users of user equipment devices inside and outside a home can use their media guidance application to communicate directly with content source 516 to access content. Specifically, within a home, users of user television equipment 502 and user computer equipment 504 may access the media guidance application to navigate among and locate desirable content. Users may also access the media guidance application outside of the home using wireless user communications devices 506 to navigate among and locate desirable content.

In a fourth approach, user equipment devices may operate in a cloud computing environment to access cloud services. In a cloud computing environment, various types of computing services for content sharing, storage or distribution (e.g., video sharing sites or social networking sites) are provided by a collection of network-accessible computing and storage resources, referred to as "the cloud." For example, the cloud can include a collection of server computing devices, which may be located centrally or at distributed locations, that provide cloud-based services to various types of users and devices connected via a network such as the Internet via communications network 514. These cloud resources may include one or more content sources 516 and one or more media guidance data sources 518. In addition or in the alternative, the remote computing sites may include other user equipment devices, such as user television equipment 502, user computer equipment 504, and wireless user communications device 506. For example, the other user equipment devices may provide access to a stored copy of a video or a streamed video. In such embodiments, user equipment devices may operate in a peer-to-peer manner without communicating with a central server.

The cloud provides access to services, such as content storage, content sharing, or social networking services, among other examples, as well as access to any content described above, for user equipment devices. Services can be provided in the cloud through cloud computing service providers, or through other providers of online services. For example, the cloud-based services can include a content storage service, a content sharing site, a social networking site, or other services via which user-sourced content is distributed for viewing by others on connected devices. These cloud-based services may allow a user equipment device to store content to the cloud and to receive content from the cloud rather than storing content locally and accessing locally-stored content.

A user may use various content capture devices, such as camcorders, digital cameras with video mode, audio recorders, mobile phones, and handheld computing devices, to record content. The user can upload content to a content storage service on the cloud either directly, for example, from user computer equipment 504 or wireless user communications device 506 having content capture feature. Alternatively, the user can first transfer the content to a user equipment device, such as user computer equipment 504. The user equipment device storing the content uploads the content to the cloud using a data transmission service on communications network 514. In some embodiments, the user equipment device itself is a cloud resource, and other user equipment devices can access the content directly from the user equipment device on which the user stored the content.

Cloud resources may be accessed by a user equipment device using, for example, a web browser, a media guidance application, a desktop application, a mobile application, and/or any combination of access applications of the same. The user equipment device may be a cloud client that relies on cloud computing for application delivery, or the user equipment device may have some functionality without access to cloud resources. For example, some applications running on the user equipment device may be cloud applications, i.e., applications delivered as a service over the Internet, while other applications may be stored and run on the user equipment device. In some embodiments, a user device may receive content from multiple cloud resources simultaneously. For example, a user device can stream audio from one cloud resource while downloading content from a second cloud resource. Or a user device can download content from multiple cloud resources for more efficient downloading. In some embodiments, user equipment devices can use cloud resources for processing operations such as the processing operations performed by processing circuitry described in relation to FIG. 4.

As referred herein, the term "in response to" refers to initiated as a result of. For example, a first action being performed in response to a second action may include interstitial steps between the first action and the second action. As referred herein, the term "directly in response to" refers to caused by. For example, a first action being performed directly in response to a second action may not include interstitial steps between the first action and the second action.

Figure 6:
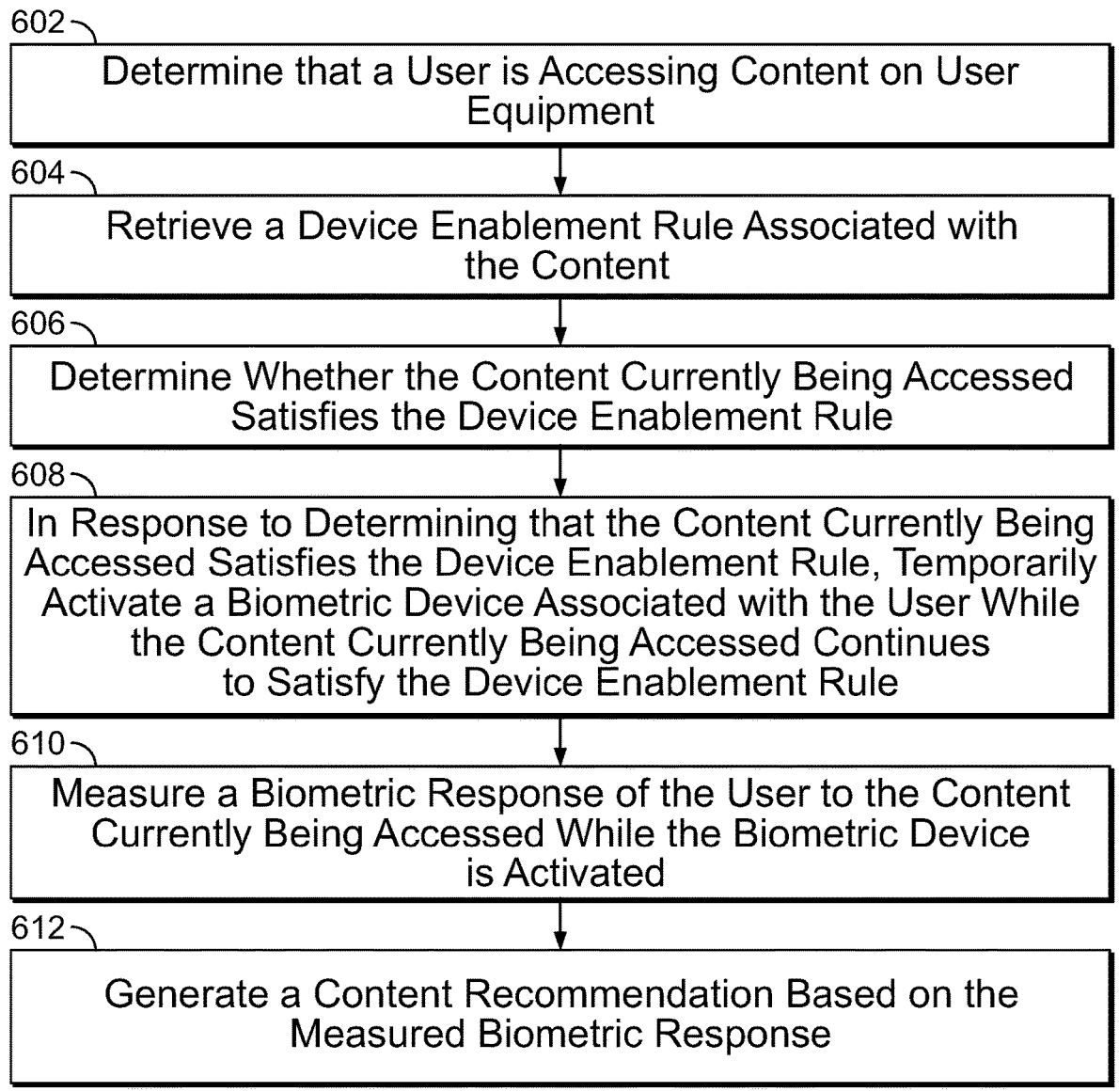
FIG. 6 is a flowchart of an illustrative process for dynamically enabling and disabling a biometric device, in accordance with some embodiments of the disclosure.

FIG. 6 is a flowchart of an illustrative process for dynamically enabling and disabling a biometric device, in accordance with some embodiments of the disclosure. It should be noted that process 600 or any step thereof could be performed on, or provided by, any of the devices shown in FIGS. 4-5. For example, process 600 may be executed by control circuitry 404 (FIG. 4) as instructed by a media guidance application implemented on a user device (e.g., user equipment devices 502, 504, and/or 506 (FIG. 5)) in order to dynamically enable and disable a biometric device. In addition, one or more steps of process 600 may be incorporated into or combined with one or more steps of any other process or embodiment (e.g., as described in relation to FIGS. 1A, 1B, and 7-13).

At step 602, control circuitry 404 (FIG. 4) determines that a user is accessing content on user equipment. The user equipment may be user television equipment 502, user computer equipment 504, and/or wireless communications device 506 (FIG. 5). Control circuitry 404 may retrieve the content from the media content source 516 and may generate, for display, on display 412. Suppose that the user is viewing the horror movie "The Conjuring." It should be noted that the content being accessed by the user may be any media including, but not limited to, videos, audio, graphics and/or games.

At step 604, control circuitry 404 (FIG. 4) retrieves a device enablement rule associated with the content. Control circuitry 404 may refer to the media guidance data source 418 to retrieve metadata associated with the content being accessed. The metadata may include device enablement rules associated with the content. For example, each scene of the movie may be associated with a device enablement rule created by the content provider. Accordingly, the metadata may include a list of scenes that details the name of a scene, the time the scene starts in the movie, information about the content in the scene, a device enablement rule, and the rule's compatibility with various biometric devices. Suppose that control circuitry 404 determines that "The Conjuring" has seventy scenes. Furthermore, based on the metadata of the movie, control circuitry 404 determines that scene two has a device enablement rule associated with the Fitbit band and various heart rate monitors. The device enablement rule may prompt the biometric device to monitor the user's heart rate throughout the duration of playback of scene two. In addition, the device enablement rule may contain information about an expected biometric response (e.g., an exciting scene in a movie may be expected to cause an accelerated heart rate).

At step 606, control circuitry 404 (FIG. 4) determines whether the content currently being accessed satisfies the device enablement rule. As previously mentioned, the metadata of the content may include information about the device enablement rule, and the rule's compatibility with various biometric devices. More specifically the compatibility information may include a list of biometric devices that are associated with the device enablement rule. In addition, control circuitry 404 may determine that the user has begun viewing scene two of "The Conjuring." Furthermore, control circuitry 404 may determine that the user is using a biometric device (e.g., Fitbit band) that is in the list of biometric devices. In some embodiments, control circuitry 404 may determine whether the biometric device is being used by the user. For example, control circuitry 404 may communicate with the user's Fitbit band to determine whether the user is wearing the band. Control circuitry 404 may also issue discovery commands to all devices in the household or within range of the display device over communication network 514 (FIG. 5). It should be noted that biometric devices usually have a built-in sensor to determine whether the user is in contact with the biometric device. If the user is not near the Fitbit band (e.g., user is viewing the movie in the living room and the biometric device is in the user's bedroom), control circuitry 404 may determine that the device does not satisfy the device enablement rule because it cannot physically measure the user's heart rate if the content criteria is met. In response, control circuitry 404 may determine that the content currently being accessed satisfies the device enablement rule.

At step 608, in response to determining that the content currently being accessed satisfies the device enablement rule, control circuitry 404 (FIG. 4) temporarily activates a biometric device associated with the user while the content currently being accessed continues to satisfy the device enablement rule. The term "temporarily" indicates that the biometric device will be enabled for a set amount of time during which the device enablement rule is satisfied. Once control circuitry 404 determines that the device enablement rule is no longer being satisfied, the biometric device is disabled/deactivated. For example, control circuitry 404 may keep the Fitbit's heart rate monitoring feature active while scene two is being generated for display to the user.

At step 610, control circuitry 404 (FIG. 4) of the biometric device measures a biometric response of the user to the content currently being accessed while the biometric device is activated. Suppose that the Fitbit acquires a set of heart rate measurements every two minutes and that scene two is ten minutes in duration. While the Fitbit's heart rate monitoring feature is activated for the ten-minute duration of scene two, the Fitbit may collect six sets of heart rate measurements. Furthermore, the Fitbit may communicate with control circuitry 404 on the user's set-top box over communication network 514 (FIG. 5). For example, the Fitbit may transfer the collected heart rate measurements to the set-top box over a Bluetooth or Wi-Fi connection. Similarly, the set-top box may issue activation/deactivation commands to the Fitbit using Bluetooth or Wi-Fi.

At step 612, control circuitry 404 (FIG. 4) generates a content recommendation based on the measured biometric response. Suppose that scene two is a horror scene with multiple jump scares. The biometric response may be the set of heart rate measurements acquired by the Fitbit. The device enablement rule may indicate that the expected biometric response should be in a heart rate range of 90-100 beats per minute. Control circuitry 404 may refer to a biometrics database in storage 408 (FIG. 4) that includes information about different levels of biometric responses. The biometrics database may have a heart rate table classifying various heart rate levels. For example, 60-80 beats per minute may be classified as a normal heart rate, whereas 80-100 beats per minute may be classified as an accelerated heart rate, in the heart rate table. Control circuitry 404 may determine that the average heart rate from the six sets of measurements is 72 beats per minute. Based on the heart rate table, control circuitry 404 may therefore determine that the user's heart rate is in the normal heart rate class and is not in the expected "accelerated" class, as indicated in the expected biometric response. As a result, control circuitry 404 may search for content that can accelerate the user's heart rate. For example, the user may not find the scenes in "The Conjuring" scary and was thus unaffected by scene two. Control circuitry 404 may determine that the genre of the user's accessed content "The Conjuring" is horror. Accordingly, control circuitry 404 may determine that the user should be recommended content from the horror genre that is considered scarier. Control circuitry 404 may refer to the Internet to search for scarier movies, or may refer to media guidance data source 618 (FIG. 6) to search for content with device enablement rules associated with a "very accelerated heart rate" expected biometric response. Once control circuitry 404 has identified a list of content associated with a "very accelerated heart rate," control circuitry 404 may search for content in the list of content that is associated with the horror genre in their respective metadata. Suppose that control circuitry 404 identifies the movie "It: Chapter One" which features scenes with device enablement rules associated with "very accelerated" heart rates. Control circuitry 404 may generate for display, the recommendation, after the viewer has stopped watching "The Conjuring" on display 412 (FIG. 4), recommending "It: Chapter One." In some embodiments, control circuitry 404 may generate for display, the recommendation, on a second display screen (e.g., the user's smartphone).

It is contemplated that the steps or descriptions of FIG. 6 may be used with any other embodiment of this disclosure. In addition, the steps and descriptions described in relation to FIG. 6 may be done in alternative orders or in parallel to further the purposes of this disclosure. For example, each of these steps may be performed in any order or in parallel or substantially simultaneously to reduce lag or increase the speed of the system or method. Any of these steps may also be skipped or omitted from the process. Furthermore, it should be noted that any of the devices or equipment discussed in relation to FIGS. 4-5 could be used to perform one or more of the steps in FIG. 6.

Figure 7:
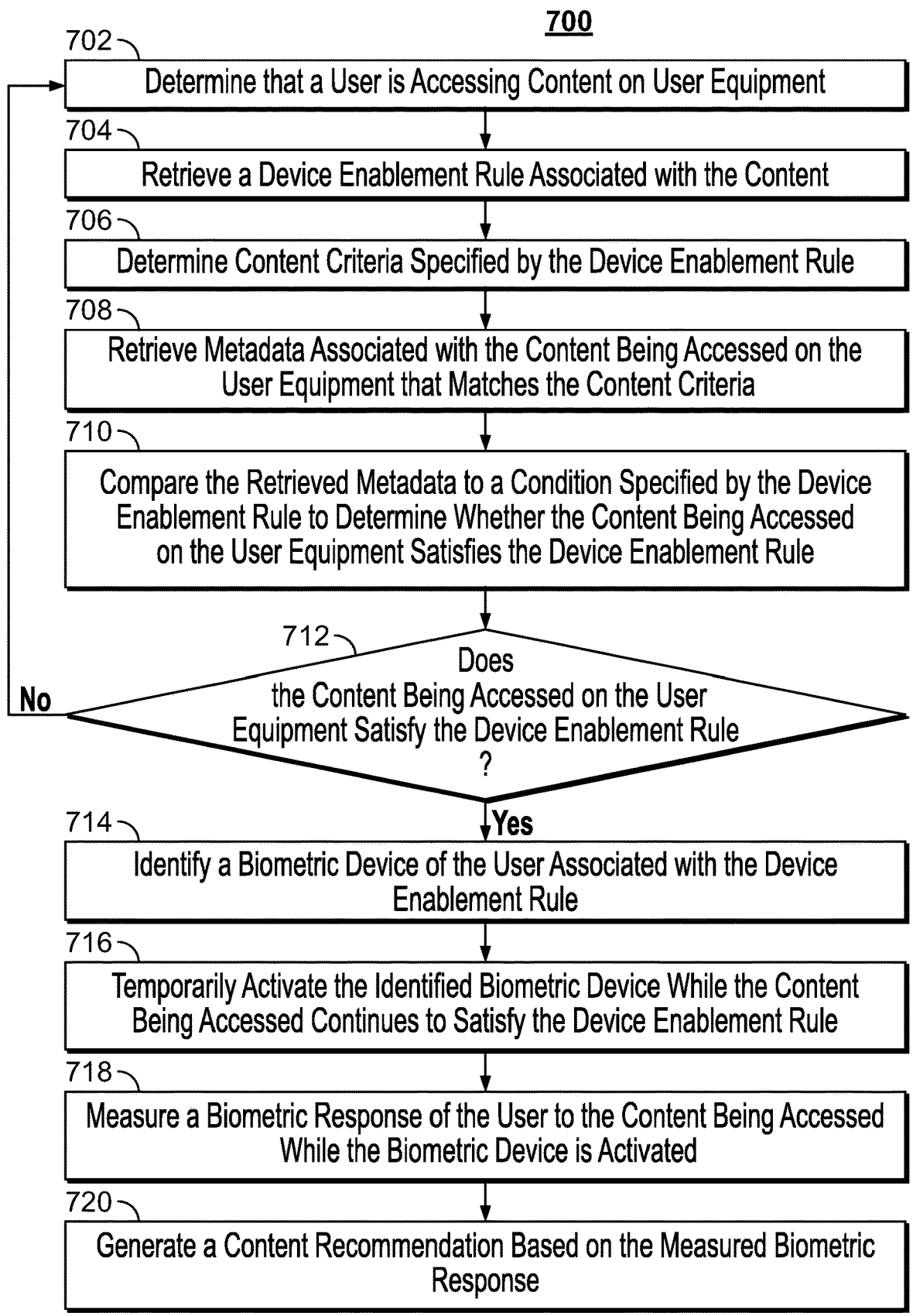
FIG. 7 is a flowchart of a detailed illustrative process for dynamically enabling and disabling a biometric device, in accordance with some embodiments of the disclosure.

FIG. 7 is a flowchart of a detailed illustrative process for dynamically enabling and disabling a biometric device, in accordance with some embodiments of the disclosure. It should be noted that process 700 or any step thereof could be performed on, or provided by, any of the devices shown in FIGS. 4-5. For example, process 700 may be executed by control circuitry 404 (FIG. 4) as instructed by a media guidance application implemented on a user device (e.g., user equipment devices 502, 504, and/or 506 (FIG. 5)) in order to dynamically enable and disable a biometric device. In addition, one or more steps of process 700 may be incorporated into or combined with one or more steps of any other process or embodiment (e.g., as described in relation to FIGS. 1A, 1B, 6, and 8-13).

At step 702, control circuitry 404 (FIG. 4) determines that a user is accessing content on user equipment. The user equipment may be user television equipment 502, user computer equipment 504, and/or wireless communications device 506 (FIG. 5). Control circuitry 404 may retrieve the content from the media content source 516 and may generate, for display, on display 412. In some embodiments, the content includes at least one of a linear media asset (e.g., television broadcast sports event), an on-demand media asset (e.g., a movie), and social chatter on a social platform associated with the user (e.g., a forum/discussion). Suppose that the user is viewing the horror movie "It: Chapter One," an on-demand media asset, on his/her set-top box.

At step 704, control circuitry 404 (FIG. 4) retrieves a device enablement rule associated with the content. Control circuitry 404 may refer to the media guidance data source 418 to retrieve metadata associated with the content being accessed. The metadata may include device enablement rules associated with the content. For example, control circuitry 404 may determine a device enablement rule that prompts biometric devices to collect heart rate measurements from the user.

In some embodiments, control circuitry 404 may generate a new device enablement rule. For example, suppose that the content provider has not added a device enablement rule to the metadata of the content. Control circuitry 404 may identify popular content, characters, topics, people, places, etc. by referring to social media (e.g., trending on Twitter). Control circuitry 404 may also identify items in the user profile in storage 408 that the user prefers (e.g., content, characters, actors, artists, places, etc.). These preferences may be explicitly stated (e.g., the user indicates that his/her favorite actor is Tom Hanks), or implicitly (e.g., the user's viewing history indicates that the user has viewed several movies featuring Tom Hanks). In response, control circuitry 404 may generate a device enablement rule with content criteria that corresponds to popularity and/or the user profile. For example, control circuitry 404 may determine that the user likes to listen to songs by Adele from the user profile. Control circuitry 404 may also determine that a new song sung by Adele is trending on Twitter. In response, control circuitry 404 may generate a device enablement rule that enables a heart rate monitor to take heart rate measurements when the user listens to the new song sung by Adele.

In some embodiments, control circuitry 404 (FIG. 4) may allow the user to create device enablement rules. For example, control circuitry 404 may allow the user to access a list of device enablement rules in the user profile in storage 408 (FIG. 4) and allow the user to manually add device enablement rules. The user may enter the device enablement rule through I/O Path 402 (FIG. 4). Control circuitry 404 may parse the user-generated device enablement rule to ensure that the user's device enablement rule is valid. For example, if a user creates the device enablement rule for measuring heart rate and associates it with a pedometer which cannot measure heart rate, control circuitry 404 may prompt the user on display 412 (FIG. 4) that the user-generated device enablement rule is not valid. Similarly, if the user creates a device enablement rule that disables a device and takes heart rate measurements, control circuitry 404 may determine that the logic of disabling a biometric device and taking a measurement is flawed because the device is not enabled. Therefore, the user's device enablement rule is not valid. Control circuitry 404 may also monitor the validity of any device enablement rule for which control circuitry 404 determines whether the content criteria is met.

At step 706, control circuitry 404 (FIG. 4) determines content criteria specified by the device enablement rule. A device enablement rule may be programmed with "if-else" logic. For example, the device enablement rule may be structured as "IF [Criteria 1] and/or [Criteria 2] . . . and/or [Criteria N], THEN [RESPONSE A1] and/or [RESPONSE A2] . . . and/or [RESPONSE AN]; ELSE [RESPONSE B1] and/or [RESPONSE B1] . . . and/or [RESPONSE BN]." In this structure, if a combination of the criteria, as established by the content provider or user, is met, control circuitry 404 will execute the respective response combination from the A set (e.g., A1, A2, etc.). If the combination of the criteria is not met, control circuitry 404 will execute the respective response combination from the B set (e.g., B1, B2, etc.). Suppose that the content provider established the device enablement rule states "IF Pennywise the Clown appears in a scene, THEN enable the biometric device and prompt the biometric device to take a heart rate measurement; ELSE disable the biometric device." Suppose that the biometric device is the Fitbit. The content criteria in this device enablement rule is the appearance of Pennywise the Clown, a character in "It: Chapter One," in a scene of the movie.

At step 708, control circuitry 404 (FIG. 4) retrieves metadata associated with the content being accessed on the user equipment that matches the content criteria. Control circuitry 404 may refer to the metadata associated with the movie, as retrieved from the media guidance data source 618 (FIG. 6) to determine the characters that appear in the movie at various playback positions (e.g., Pennywise the Clown). Control circuitry 404 may also use computer vision to identify objects on the screen and classify whether the object is Pennywise the Clown or not, using a reference image of Pennywise the Clown (e.g., retrieved from the Internet). Control circuitry 404 may refer to the subtitles of the movie to determine when Pennywise the Clown is mentioned in the movie. Control circuitry 404 may also analyze the audio of the movie and utilize natural language processing to identify the voice of Pennywise the Clown, using a reference voice model of Pennywise the Clown (e.g., retrieved from the Internet). Using any combination of these processes, control circuitry 404 may identify the appearance of Pennywise the Clown and determine that the content criteria is met.

In some embodiments, the device enablement rule may specify the playback positions in which Pennywise the Clown appears in the movie. For example, the device enablement rule may state "IF playback is at position 0:12:57 or 0:50:12 or 1:24:23, THEN enable the biometric device and prompt the biometric device to take a heart rate measurement; ELSE disable the biometric device." The content criteria in this case points to specific playback positions in the movie, such as 12 minutes and 57 seconds from the start (e.g., 0:12:57). Once playback to the user reaches this point, the content criteria may be satisfied.

At step 710, control circuitry 404 (FIG. 4) compares the retrieved metadata to a condition specified by the device enablement rule, to determine whether the content being accessed on the user equipment satisfies the device enablement rule. For example, if the user is on playback position 0:12:57, control circuitry 404 may determine that the content criteria of the device enablement rule is satisfied. In contrast, if the user is on playback position 0:05:11, control circuitry 404 may determine that the content criteria of the device enablement rule is not satisfied.

At step 712, control circuitry 404 (FIG. 4) determines whether the content being accessed on the user equipment satisfies the device enablement rule and furthers the process accordingly. If the content does not satisfy the device enablement rule, the process returns to step 702 and control circuitry 404 determines a new playback position of the content being accessed by the user. If the content satisfies the device enablement rule, control circuitry 404 forwards the process to step 714.

At step 714, control circuitry 404 (FIG. 4) identifies a biometric device of the user associated with the device enablement rule. As previously mentioned, the device enablement rule may be retrieved from the metadata of the content. The metadata may also include information about the biometric devices that the user possesses. For example, control circuitry 404 may determine, from the metadata, that the biometric device associated with the device enablement rule (e.g., to measure heart rate) and possessed by the user include a Samsung Gear, a Fitbit band, and a portable heart rate monitor. In some embodiments, control circuitry 404 may determine whether the biometric device is being used by the user. For example, control circuitry 404 may communicate with the user's Fitbit band to determine whether the user is wearing the band. Biometric devices usually have a built-in sensor to determine whether the user is in contact with the biometric device. If the user is not near the Fitbit band (e.g., user is viewing the movie in the living room and the biometric device is in the user's bedroom), control circuitry 404 may determine that the device does not satisfy the device enablement rule because it cannot physically measure the user's heart rate if the content criteria is met.

At step 716, control circuitry 404 (FIG. 4) temporarily activates the identified biometric device while the content being accessed continues to satisfy the device enablement rule. Returning to the overarching example, control circuitry 404 may identify that the user is wearing his/her Fitbit band. In addition, control circuitry 404 may determine that Pennywise the Clown has appeared in a scene being viewed by the user. In response, control circuitry 404 may determine that the content criteria of the device enablement rule have been satisfied, and may enable the biometric device. The user's Fitbit may remain enabled until Pennywise the Clown exits the scene. Suppose that the user's Fitbit was initially in a deactivated state. For example, the data acquisition of the Fitbit may have been stopped, or the Fitbit was in sleep mode, a lower power mode, or completely powered down. During activation, the Fitbit's data acquisition may be started, the Fitbit may be transferred to an active mode, or the Fitbit may be powered on.

At step 718, control circuitry 404 (FIG. 4) measures a biometric response of the user to the content being accessed while the biometric device is activated. For example, while Pennywise the Clown is in the scene being viewed by the user, control circuitry 404 may ensure that the user's Fitbit band is active, and is collecting the user's heart rate. In some embodiments, control circuitry 404 may store this biometric response (e.g., heart rate values organized with time stamps) in storage 408 (FIG. 4). Control circuitry 404 may determine that during the duration in which the Fitbit was enabled, the average heart rate of the user was 111 beats per minute.

At step 720, control circuitry 404 (FIG. 4) generates a content recommendation based on the measured biometric response. Suppose that in a certain scene, Pennywise the Clown appears. Metadata associated with the device enablement rule may indicate that the expected biometric response should be in a heart rate range of 90-100 beats per minute. Control circuitry 404 may refer to a biometrics database in storage 408 (FIG. 4) that includes information about different levels of biometric responses. As previously mentioned, the biometrics database may have a heart rate table classifying various heart rate levels. For example, 80-100 beats per minute may be classified as an accelerated heart rate and 100-120 may be classified as very accelerated, in the heart rate table. Based on the heart rate table, control circuitry 404 may therefore determine that the user's heart rate is in the "very accelerated" heart rate class and is not in the expected "accelerated" class, as indicated in the expected biometric response. In some embodiments, if the user's biometric response increases beyond a threshold (e.g., 140 beats per minute), control circuitry 404 may stop playback of the content being accessed by the user as a safety measure. This is further discussed in the description of FIG. 13. In some embodiments, control circuitry 404 may search for content that can slow down the user's heart rate. Control circuitry 404 may determine that the genre of the user's accessed content "It: Chapter One" is horror. Accordingly, control circuitry 404 may determine that the user should be recommended content from the horror genre that is considered less scary. Control circuitry 404 may refer to the Internet to search for horror movies, or may refer to media guidance data source 618 (FIG. 6) to search for content with device enablement rules associated with a "slightly-accelerated heart rate" expected biometric response. Once control circuitry 404 has identified a list of content associated with a "slightly accelerated heart rate," control circuitry 404 may search for content in the list of content that is associated with the horror genre in their respective metadata. Suppose that control circuitry 404 identifies the movie "The Conjuring" which features scenes with device enablement rules associated with maximum "slightly accelerated" heart rates. Control circuitry 404 may generate for display, the recommendation, after the viewer has stopped watching "It: Chapter One" on display 412 (FIG. 4), recommending "The Conjuring." In some embodiments, control circuitry 404 may generate for display, the recommendation, on a second display screen (e.g., the user's smartphone).

It is contemplated that the steps or descriptions of FIG. 7 may be used with any other embodiment of this disclosure. In addition, the steps and descriptions described in relation to FIG. 7 may be done in alternative orders or in parallel to further the purposes of this disclosure. For example, each of these steps may be performed in any order or in parallel or substantially simultaneously to reduce lag or increase the speed of the system or method. Any of these steps may also be skipped or omitted from the process. Furthermore, it should be noted that any of the devices or equipment discussed in relation to FIGS. 4-5 could be used to perform one or more of the steps in FIG. 7.

Figure 8:
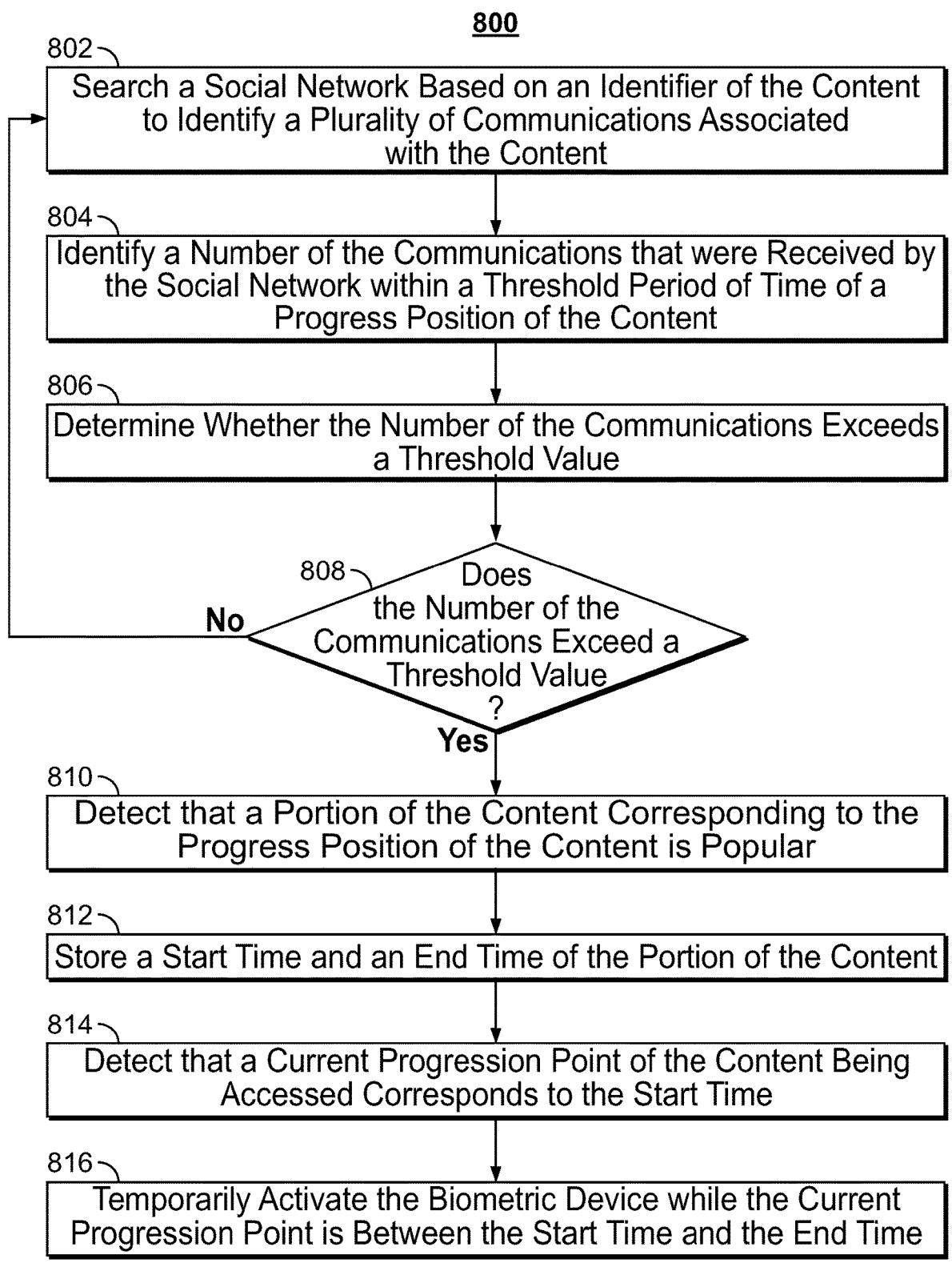
FIG. 8 is a flowchart of a detailed illustrative process for determining whether a portion of the content corresponding to a progress position of the content is popular, in accordance with some embodiments of the disclosure.

FIG. 8 is a flowchart of a detailed illustrative process for determining whether a portion of the content corresponding to a progress position of the content is popular, in accordance with some embodiments of the disclosure. It should be noted that process 800 or any step thereof could be performed on, or provided by, any of the devices shown in FIGS. 4-5. For example, process 800 may be executed by control circuitry 404 (FIG. 4) as instructed by a media guidance application implemented on a user device (e.g., user equipment devices 502, 504, and/or 506 (FIG. 5)) in order to determine whether a portion of the content corresponding to a progress position of the content is popular. In addition, one or more steps of process 800 may be incorporated into or combined with one or more steps of any other process or embodiment (e.g., as described in relation to FIGS. 1A, 1B, 6-7, and 9-13).

At step 802, control circuitry 404 (FIG. 4) searches a social network based on an identifier of the content to identify a plurality of communications associated with the content. The identifier of the content may be any representation of the content such as the content's name (e.g., "It: Chapter Name"), common name (e.g., "It"), genre (e.g., horror), creator (e.g., artist, production house, director, etc.), characters, cast, artwork, and/or sound. Accordingly, control circuitry 404 may search for "Pennywise the Clown" on a social network such as Facebook, in order to identify a plurality of communications associated with "Pennywise the Clown." The plurality of communications may include posts, comments, messages, acknowledgments (e.g., likes, reactions, etc.), videos, photos, audio clips, etc.

At step 804, control circuitry 404 (FIG. 4) identifies a number of the communications that were received by the social network within a threshold period of time of a progress position of the content. The threshold period of time may be a window of time before and/or after the progress position of the content. The progress position represents a discrete point in the content and may include, but is not limited to, the playback position of a video/audio or a slide number in a slideshow of images and text. Suppose that the progress point is 12 min 50 seconds into the movie "It: Chapter One" and the threshold period of time is ten minutes. Control circuitry 404 may thus only consider communications that were received by the social network, Facebook, between 7 min 50 seconds and 17 min 50 seconds. In some cases, control circuitry 404 may consider a shifted window of time. For example, control circuitry 404 may consider communications between 4 min 50 second and 14 min 50 seconds. In this case, the ten-minute threshold period of time is not centered at the progress point. Thus, any communications referring to scenes within the threshold period of time of the progress point may be considered. For example, while accessing "It: Chapter One," a first user (e.g., the user's friend) may post a comment on a social network. Control circuitry 404 on the friend's device may determine that the friend is accessing "It: Chapter One" and add the friend's progress point as metadata to the friend's communication. When control circuitry 404 on the user's device identifies communications, control circuitry 404 may retrieve the metadata of the communication to determine whether the communication's progress point is within the threshold period of time. In the case where the user is accessing content being broadcasted, control circuitry 404 may determine the transmission time of the content and consider the progress point with respect to the transmission time. For example, if "It: Chapter One" is broadcasted on HBO on Nov. 1, 2017 at 8:00 pm, and the progress point is 12 min 50 seconds into the movie, control circuitry 404 may consider commercial times and content version in order to determine that the progress point time is 8:15 pm. Thus, the threshold period of time may be any ten-minute window around 8:15 pm (e.g., 8:12 pm and 8:22 pm). As a result, control circuitry 404 may consider communications that were received by a social network during that time.

At step 806, control circuitry 404 (FIG. 4) determines whether the number of the communications exceeds a threshold value. For example, control circuitry 404 may count the number of communications that were received within a threshold period of time by various social networks (e.g., Facebook, Twitter, Instagram, Reddit, etc.) and are associated with the identifier of the content. Suppose that control circuitry 404 identifies 10,000 communications. In some embodiments, the user may also limit the communications to those posted by the user's friends. In this case, control circuitry 404 may identify 50 communications. Control circuitry 404 may retrieve a threshold value from the user profile in storage 408. The threshold value (e.g., 20) represents a minimum amount of communications needed to determine whether the portion of the content is popular.

At step 808, control circuitry 404 (FIG. 4) decides whether the number of the communications exceed a threshold value. If the number of communications is less than the threshold value, the process returns to step 802. At this point, the user's progress point may have changed. Therefore, control circuitry 404 may identify new communications on a social network. If the number of communications is greater than the threshold value, the process continues to step 810.

At step 810, control circuitry 404 (FIG. 4) detects that a portion of the content corresponding to the progress position of the content is popular. For example, the threshold value may be 20 and the number of communications may be 50. Accordingly, control circuitry 404 may determine that the portion within the threshold period of time is popular.

At step 812, control circuitry 404 (FIG. 4) stores a start time and an end time of the portion of the content. The start time may be the first time of the window of time formed by the threshold period of time around the progress point. The end time may the last time of the window of time formed by the threshold period of time around the progress point. For example, if the progress point is 12 min 50 seconds, and the threshold period of time is ten minutes, the start time may be 7 min 50 seconds and the end time may be 17 min 50 seconds. In terms of transmission time (e.g., content began transmission at 8:00 pm on HBO), the start time may be 8:08 pm and the end time may be 8:18 pm.

At step 814, control circuitry 404 (FIG. 4) detects that a current progression point of the content being accessed corresponds to the start time. Consider a scenario in which the progress point is 12 minutes 50 seconds. The threshold window of time may ten minutes. Furthermore, the ten-minute window may start at 12 minutes 50 seconds (e.g., start time) and end at 22 minutes 50 seconds (e.g., end time). Control circuitry 404 may determine that the current progression point of the content (e.g., 12 minutes 55 seconds) corresponds to the start time and is within the threshold period of time. Control circuitry 404 may determine that the current progression time corresponds to the start time if the current progression time is within second threshold period of time from the start time. The second threshold period of time is less than the threshold period of time discussed previously (e.g., within 10 seconds from the start time).

At step 816, control circuitry 404 (FIG. 4) temporarily activates the biometric device while the current progression point is between the start time and the end time. For example, control circuitry 404 may communicate with the user's Fitbit band to enable the Fitbit's heart rate measuring feature at the start time. Once the current progression point has reached the end time, control circuitry 404 may communicate with the user's Fitbit band to disable the Fitbit's heart rate measuring feature.

It is contemplated that the steps or descriptions of FIG. 8 may be used with any other embodiment of this disclosure. In addition, the steps and descriptions described in relation to FIG. 8 may be done in alternative orders or in parallel to further the purposes of this disclosure. For example, each of these steps may be performed in any order or in parallel or substantially simultaneously to reduce lag or increase the speed of the system or method. Any of these steps may also be skipped or omitted from the process. Furthermore, it should be noted that any of the devices or equipment discussed in relation to FIGS. 4-5 could be used to perform one or more of the steps in FIG. 8.

Figure 9:
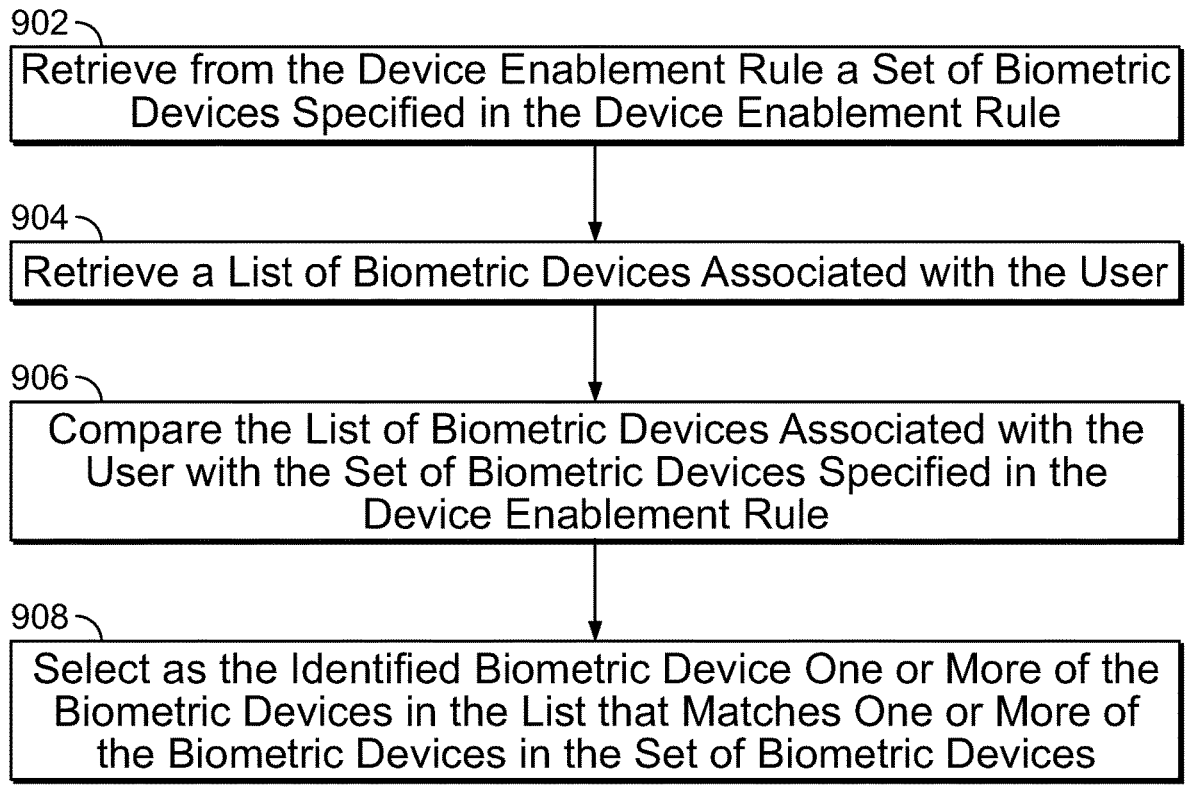
FIG. 9 is a flowchart of a detailed illustrative process for comparing a list of biometric devices associated with the user with a set of biometric devices specified in the device enablement rule, in accordance with some embodiments of the disclosure.

FIG. 9 is a flowchart of a detailed illustrative process for determining whether a portion of the content corresponding to a progress position of the content is popular, in accordance with some embodiments of the disclosure. It should be noted that process 900 or any step thereof could be performed on, or provided by, any of the devices shown in FIGS. 4-5. For example, process 900 may be executed by control circuitry 404 (FIG. 4) as instructed by a media guidance application implemented on a user device (e.g., user equipment devices 502, 504, and/or 506 (FIG. 5)) in order to determine whether a portion of the content corresponding to a progress position of the content is popular. In addition, one or more steps of process 900 may be incorporated into or combined with one or more steps of any other process or embodiment (e.g., as described in relation to FIGS. 1A, 1B, 6-8, and 10-13).

At step 902, control circuitry 404 (FIG. 4) retrieves from the device enablement rule, a set of biometric devices specified in the device enablement rule. For example, control circuitry 404 may refer to the media guidance data source 518 (FIG. 5) to retrieve metadata associated with the device enablement rule. The metadata may include a set of biometric devices that the device enablement rule specifies. For example, the set of biometric devices associated with the device enablement rule that measures heart rate may include Fitbit bands, Samsung Gear, and a portable heart rate monitor.

At step 904, control circuitry 404 (FIG. 4) retrieves a list of biometric devices associated with the user. As previously mentioned, control circuitry 404 may refer to the user profile in storage 408 (FIG. 4) to identify biometric devices that the user has access to, or is associated with the user. For example, control circuitry 404 may determine that the user is associated with a Fitbit band, a Samsung Gear, and a pedometer.

At step 906, control circuitry 404 (FIG. 4) compares the list of biometric devices associated with the user with the set of biometric devices specified in the device enablement rule. For example, control circuitry 404 may determine that the device enablement rule is associated with the Fitbit band and the Samsung Gear, two devices that the user is associated with. However, control circuitry 404 may also determine that the user is not associated with a portable heart rate monitor, and the device enablement rule is not compatible with the pedometer.

At step 908, control circuitry 404 (FIG. 4) selects as the identified biometric device, one or more of the biometric devices in the list that matches one or more of the biometric devices in the set of biometric devices. For example, control circuitry 404 may select the Fitbit band and the Samsung Gear because they appear in both the list and the set of biometric devices.

It is contemplated that the steps or descriptions of FIG. 9 may be used with any other embodiment of this disclosure. In addition, the steps and descriptions described in relation to FIG. 9 may be done in alternative orders or in parallel to further the purposes of this disclosure. For example, each of these steps may be performed in any order or in parallel or substantially simultaneously to reduce lag or increase the speed of the system or method. Any of these steps may also be skipped or omitted from the process. Furthermore, it should be noted that any of the devices or equipment discussed in relation to FIGS. 4-5 could be used to perform one or more of the steps in FIG. 9.

Figure 10:
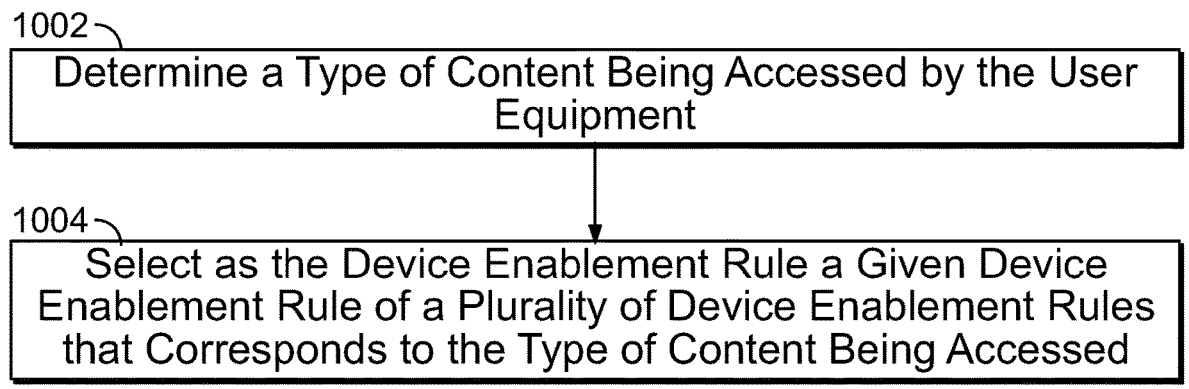
FIG. 10 is a flowchart of a detailed illustrative process for determining a type of content being accessed by the user equipment, in accordance with some embodiments of the disclosure.

FIG. 10 is a flowchart of a detailed illustrative process for determining a type of content being accessed by the user equipment, in accordance with some embodiments of the disclosure. It should be noted that process 1000 or any step thereof could be performed on, or provided by, any of the devices shown in FIGS. 4-5. For example, process 1000 may be executed by control circuitry 404 (FIG. 4) as instructed by a media guidance application implemented on a user device (e.g., user equipment devices 502, 504, and/or 506 (FIG. 5)) in order to determine a type of content being accessed by the user equipment. In addition, one or more steps of process 1000 may be incorporated into or combined with one or more steps of any other process or embodiment (e.g., as described in relation to FIGS. 1A, 1B, 6-9, and 11-13).

At step 1002, control circuitry 404 (FIG. 4) determines a type of content being accessed by the user equipment. The type of content may be the medium in which the content is presented. For example, the content may be a video, an audio clip, an e-book, an image, a game, etc. Control circuitry 404 may refer to the metadata of the content, retrieve from the media guidance data source 518 (FIG. 5), to determine the type of content.

At step 1004, control circuitry 404 (FIG. 4) selects as the device enablement rule, a given device enablement rule of a plurality of device enablement rules that corresponds to the type of content being accessed. For example, the user may be able to access the content "It: Chapter One" in various types. These types include a video of the movie, an audiobook, an e-book of the original story written by Stephen King, or a comic featuring various graphics. Depending on the type of content, the device enablement rules may vary. For example, for a video, the device enablement rule may activate a biometric device in response to determining that Pennywise the Clown has appeared in a scene. For the audiobook, a device enablement rule may activate whenever a voice actor portraying Pennywise the Clown speaks. Control circuitry 404 may thus select a device enablement rule from a plurality of device enablement rules, based on the type of content the user is accessing.

It is contemplated that the steps or descriptions of FIG. 10 may be used with any other embodiment of this disclosure. In addition, the steps and descriptions described in relation to FIG. 10 may be done in alternative orders or in parallel to further the purposes of this disclosure. For example, each of these steps may be performed in any order or in parallel or substantially simultaneously to reduce lag or increase the speed of the system or method. Any of these steps may also be skipped or omitted from the process. Furthermore, it should be noted that any of the devices or equipment discussed in relation to FIGS. 4-5 could be used to perform one or more of the steps in FIG. 10.

Figure 11:
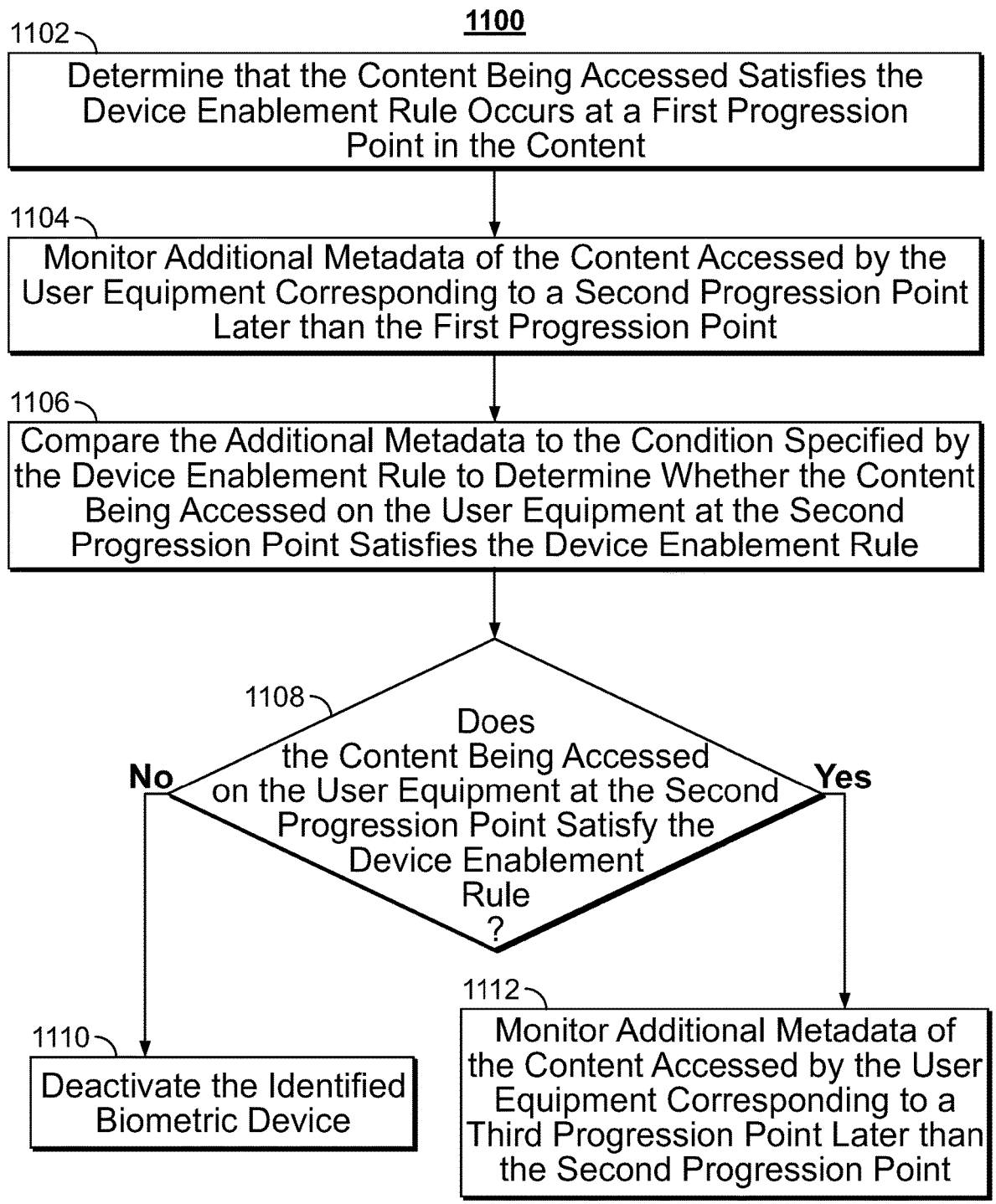
FIG. 11 is a flowchart of a detailed illustrative process for deactivating the identified biometric device, in accordance with some embodiments of the disclosure.

FIG. 11 is a flowchart of a detailed illustrative process for deactivating the identified biometric device, in accordance with some embodiments of the disclosure. It should be noted that process 1100 or any step thereof could be performed on, or provided by, any of the devices shown in FIGS. 4-5. For example, process 1100 may be executed by control circuitry 404 (FIG. 4) as instructed by a media guidance application implemented on a user device (e.g., user equipment devices 502, 504, and/or 506 (FIG. 5)) in order to deactivate the identified biometric device. In addition, one or more steps of process 1100 may be incorporated into or combined with one or more steps of any other process or embodiment (e.g., as described in relation to FIGS. 1A, 1B, 6-10, and 12-13).

At step 1102, control circuitry 404 (FIG. 4) determines that the content being accessed satisfies the device enablement rule, occurs at a first progression point in the content. If a user is accessing "It: Chapter One" in the form of an audiobook, control circuitry 404 may retrieve a device enablement rule that states "IF the voice actor of Pennywise the Clown speaks, THEN enable the biometric device and measure the user's heart rate; ELSE disable the biometric device." Control circuitry 404 may use voice recognition method (e.g., natural language processing) to identify that the voice actor of Pennywise the Clown begins talking 12 minutes and 50 seconds from the start of the content. Control circuitry 404 may also refer to metadata associated with the audiobook that indicates the times at which various voice actors speak. If the user's current playback position is the first progression point, control circuitry 404 may check whether the device enablement rule is satisfied. Suppose that the user's first progression point is 12 minutes 50 seconds. Control circuitry 404 may determine that the device enablement rule is satisfied.

At step 1104, control circuitry 404 (FIG. 4) monitors additional metadata of the content accessed by the user equipment corresponding to a second progression point later than the first progression point. For example, control circuitry 404 may determine that the use has reached a second progression point (e.g., 13 minutes 35 seconds). At that point, control circuitry 404 may monitor the metadata associated with the audiobook to determine the voice actors that are speaking during the second progression point. Suppose that the voice actor for Pennywise the Clown stops speaking at the second progression point.

At step 1106, control circuitry 404 (FIG. 4) compares the additional metadata to the condition specified by the device enablement rule to determine whether the content being accessed on the user equipment at the second progression point satisfies the device enablement rule. If the device enablement rule measures heart rate when the voice actor of Pennywise the Clown speaks, control circuitry 404 may determine that the voice actor stops speaking at the second progression point. As a result, the device enablement rule is not satisfied.

At step 1108, control circuitry 404 (FIG. 4) decides whether the content being accessed on the user equipment at the second progression point satisfies the device enablement rule. If the device enablement rule is not satisfied, the process continues to step 1110. Otherwise, the process continues to step 1112.

At step 1110, control circuitry 404 (FIG. 4) deactivates the identified biometric device. For example, if the Fitbit band of the user begins taking heart rate measurements from the first progression point, control circuitry 404 may communicate with the Fitbit band over communication network 514 (FIG. 5) in order to deactivate the Fitbit band. As a result, the Fitbit band will stop taking heart rate measurements.

At step 1112, in response to determining that the device enablement rule is satisfied, control circuitry 404 (FIG. 4) monitors additional metadata of the content accessed by the user equipment corresponding to a third progression point later than the second progression point. For example, control circuitry 404 may wait an additional period of time until the user reaches the third progression point (e.g., 15 minutes 2 seconds). Once the user has reached the third progression point, control circuitry 404 may access metadata associated with the third progression point, such as the name(s) of the voice actors speaking at the third progression point. This serves the purpose of determining a point at which the device enablement rule is no longer satisfied.

It is contemplated that the steps or descriptions of FIG. 11 may be used with any other embodiment of this disclosure. In addition, the steps and descriptions described in relation to FIG. 11 may be done in alternative orders or in parallel to further the purposes of this disclosure. For example, each of these steps may be performed in any order or in parallel or substantially simultaneously to reduce lag or increase the speed of the system or method. Any of these steps may also be skipped or omitted from the process. Furthermore, it should be noted that any of the devices or equipment discussed in relation to FIGS. 4-5 could be used to perform one or more of the steps in FIG. 11.

Figure 12:
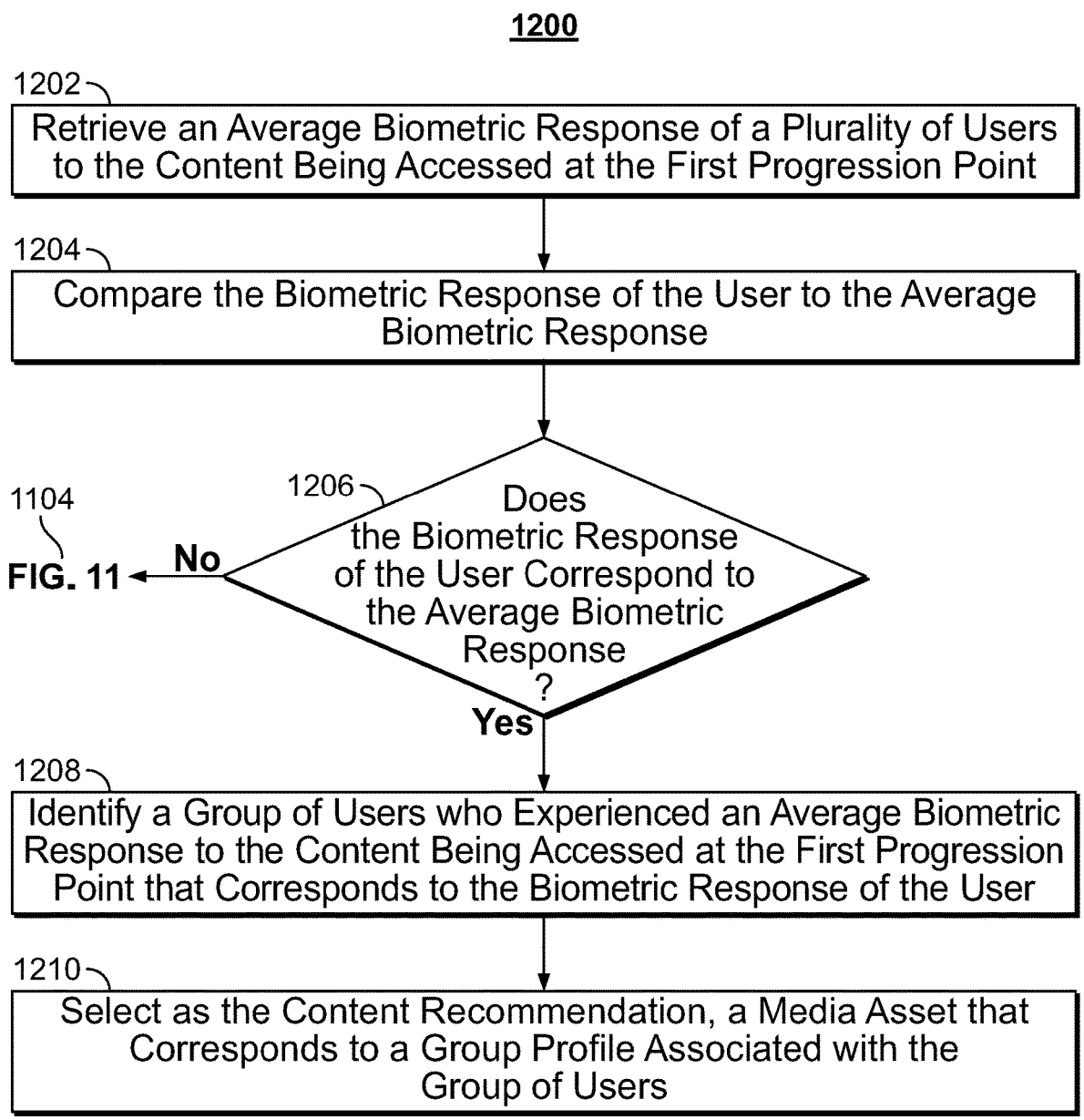
FIG. 12 is a flowchart of a detailed illustrative process for selecting a media asset, as the content recommendation, that corresponds to a group profile associated with a group of users, in accordance with some embodiments of the disclosure.

FIG. 12 is a flowchart of a detailed illustrative process for selecting a media asset, as the content recommendation, that corresponds to a group profile associated with a group of users, in accordance with some embodiments of the disclosure. It should be noted that process 1200 or any step thereof could be performed on, or provided by, any of the devices shown in FIGS. 4-5. For example, process 1200 may be executed by control circuitry 404 (FIG. 4) as instructed by a media guidance application implemented on a user device (e.g., user equipment devices 502, 504, and/or 506 (FIG. 5)) in order to select a media asset, as the content recommendation, that corresponds to a group profile associated with a group of users. In addition, one or more steps of process 1200 may be incorporated into or combined with one or more steps of any other process or embodiment (e.g., as described in relation to FIGS. 1A, 1B, 6-11, and 13).

At step 1202, control circuitry 404 (FIG. 4) retrieves an average biometric response of a plurality of users to the content being accessed at the first progression point. For example, control circuitry 404 may refer to a remote server that stores biometric responses of various users through communication network 514 (FIG. 5). The remote server may include a biometrics database that is organized based on various measurements and biometric devices. For example, the biometrics database may include heart rate measurements of various users. The heart rate measurements may be associated with content, progression points, and other details (e.g., biometrics) about users such as age and weight. Control circuitry 404 may retrieve the heart rate measurements for a plurality of users listed in the biometrics database that accessed "It: Chapter One" in the same content type as the user. More specifically, control circuitry 404 may determine whether the biometric response is associated with the first progression point. If so, control circuitry 404 may determine the average biometric response. For example, if control circuitry 404 retrieves 10,000 heart rate measurements associated with "It: Chapter One" (e.g., audiobook) at the first progression point (e.g., 12 minutes 50 seconds), control circuitry 404 may determine that the average heart rate is 82 beats per minute.

At step 1204, control circuitry 404 (FIG. 4) compares the biometric response of the user to the average biometric response. Suppose that the biometric response of the user at the first progression point was 80 beats per minute. Control circuitry 404 may rely on a response threshold to compare the user's biometrics response with the average biometrics response. The response threshold represents a range within which the biometric response may correspond. For example, the response threshold for heart rate measurements may be 5 beats per minute. Therefore, if the biometric response of the user is plus or minus 5 beats per minute within range of the average biometric response (e.g., between 77 beats per minute and 87 beats per minute), control circuitry 404 may determine that the biometric response corresponds to the average biometric response. In some cases, the response threshold is determined by a percentage difference. For example, the response threshold may be 2%. Therefore, control circuitry 404 may determine that the range of the average heart rate is 2% plus or minus the heart rate (e.g., 2% of 82 is 1.64 and thus the range is between 82-1.64 beats per minute and 82+1.64 beats per minute).

At step 1206, control circuitry 404 (FIG. 4) decides whether the biometric response of the user corresponds to the average biometric response. Suppose that control circuitry 404 relies on the range method for the response threshold. Based on the response threshold of 5 beats per minute, control circuitry 404 may determine that the user's biometric response, 80 beats per minute, corresponds to the average biometric response. The process progresses to step 1208. However, if control circuitry 404 determines that the user's biometric response was 70 beats per minute (e.g., outside of the response threshold), the process may shift to step 1104 of FIG. 11. In this case, control circuitry 404 may continue to look for metadata associated with the content across various progression points.

At step 1208, control circuitry 404 (FIG. 4) identifies a group of users who experienced an average biometric response to the content being accessed at the first progression point that corresponds to the biometric response of the user. For example, control circuitry 404 may determine that of the plurality of 10,000 users identified in step 1202, 2,000 users experienced a biometric response that also corresponds to the user's biometric response. More specifically, 2,000 users have a biometric response that is within the response threshold of the user. If the user's biometric response is 80 beats per minute and the response threshold is 2 beats per minute, control circuitry 404 may identify users with an average biometric response between 78 and 82 beats per minute.

At step 1210, control circuitry 404 (FIG. 4) selects as the content recommendation, a media asset that corresponds to a group profile associated with the group of users. For example, control circuitry 404 may determine that out of the 10,000 users identified in step 1202, 2,000 users have biometric responses corresponding to the user's biometric response. Control circuitry 404 may classify the 2,000 users under a group profile. For example, control circuitry 404 may access the user profiles of the respective users to determine commonalities of interest (e.g., favorite movies, most accessed media asset, etc.). Based on this information, control circuitry 404 may recommend a media asset that a majority of the users have accessed or favorited.

It is contemplated that the steps or descriptions of FIG. 12 may be used with any other embodiment of this disclosure. In addition, the steps and descriptions described in relation to FIG. 12 may be done in alternative orders or in parallel to further the purposes of this disclosure. For example, each of these steps may be performed in any order or in parallel or substantially simultaneously to reduce lag or increase the speed of the system or method. Any of these steps may also be skipped or omitted from the process. Furthermore, it should be noted that any of the devices or equipment discussed in relation to FIGS. 4-5 could be used to perform one or more of the steps in FIG. 12.

Figure 13:
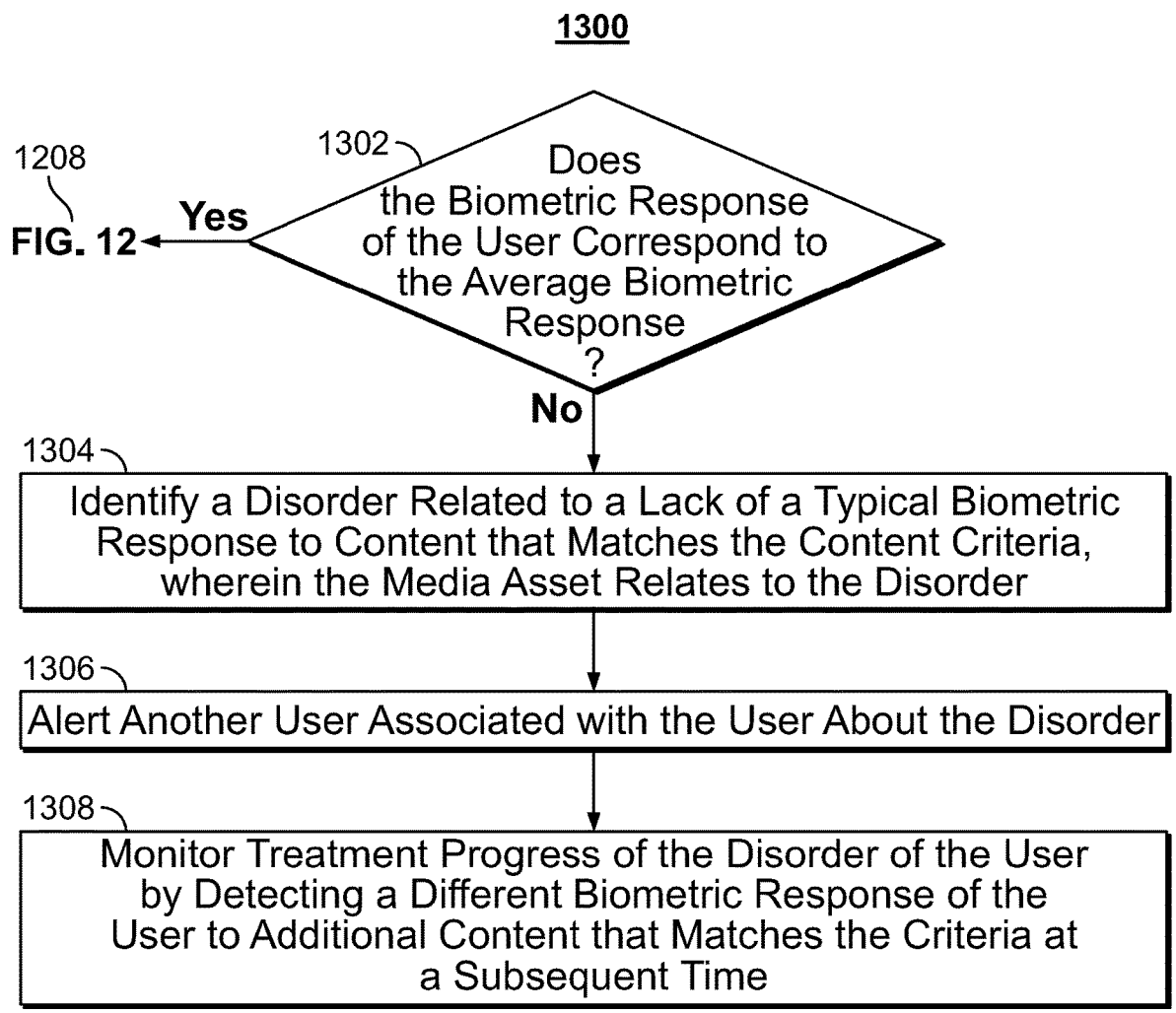
FIG. 13 is a flowchart of a detailed illustrative process for identifying a disorder related to a lack of a typical biometric response to content that matches the content criteria, in accordance with some embodiments of the disclosure.

FIG. 13 is a flowchart of a detailed illustrative process for identifying a disorder related to a lack of a typical biometric response to content that matches the content criteria, that corresponds to a group profile associated with a group of users, in accordance with some embodiments of the disclosure. It should be noted that process 1300 or any step thereof could be performed on, or provided by, any of the devices shown in FIGS. 4-5. For example, process 1300 may be executed by control circuitry 404 (FIG. 4) as instructed by a media guidance application implemented on a user device (e.g., user equipment devices 502, 504, and/or 506 (FIG. 5)) in order to identify a disorder related to a lack of a typical biometric response to content that matches the content criteria. In addition, one or more steps of process 1300 may be incorporated into or combined with one or more steps of any other process or embodiment (e.g., as described in relation to FIGS. 1A, 1B and 6-12).

At step 1302, control circuitry 404 (FIG. 4) decides whether the biometric response of the user corresponds to the average biometric response. Suppose that control circuitry 404 relies on the percentage method for the response threshold. Based on the response threshold of 4% beats per minute, control circuitry 404 may determine that the user's biometric response, 80 beats per minute, corresponds to the average biometric response. The process progresses to step 1208 in FIG. 12. However, if control circuitry 404 determines that the user's biometric response was 140 beats per minute (e.g., outside of the response threshold), the process shifts to step 1304.

At step 1304, control circuitry 404 (FIG. 4) identifies a disorder related to a lack of a typical biometric response to content that matches the content criteria, wherein the media asset relates to the disorder. Suppose that the heart rate of the user, in response to accessing content at the first progression point, rises to 140 beats per minute. In comparison to the average heart rate of the users identified in 1302 (e.g., 82 beats per minute), control circuitry 404 may determine that the user's heart rate is abnormally high. Furthermore, control circuitry 404 may refer to the biometrics database to determine whether the user's heart rate when accessing other content is consistently above the expected biometric response. For example, control circuitry 404 may determine that the user has accessed ten media assets in the past. For each media asset, control circuitry 404 may determine that a majority of the user's biometric responses exceed the expected biometric response by a threshold amount. The threshold amount may be a percentage or number indicating a minimum difference from the expected biometric response, for which the user's biometric response is considered abnormal. If the threshold percentage is 40%, the expected biometric response is 100 beats per minute and the user's biometric response is 150 beats per minute, control circuitry 404 may determine that the response's difference is 50% and therefore the measurement is abnormal. In response, control circuitry 404 may identify a heart disorder associated with very high heart rates. Control circuitry 404 may refer to the biometrics database to identify disorders associated with the user's abnormal biometric responses. As mentioned previously, the biometrics database may additionally include names of disorders, definitions, and associated values of biometric responses.

At step 1306, control circuitry 404 (FIG. 4) alert another user associated with the user about the disorder. Control circuitry 404 may refer to the user profile in storage 408 (FIG. 4) to identify emergency contacts selected by the user. For example, the user may indicate his/her parents as emergency contacts. In response to determining an abnormal biometric response, control circuitry 404 may send a message to the parents of the user indicating a potential risk for the identified disorder. The message may include, but is not limited to, a text message, an email, a social media message, or a computer voice-generated phone call.

At step 1308, control circuitry 404 (FIG. 4) monitors treatment progress of the disorder of the user by detecting a different biometric response of the user to additional content that matches the criteria at a subsequent time. For example, control circuitry 404 may increase the frequency of heart rate measurements by creating device enablement rules that measure heart rate. Control circuitry 404 may recommend content similar to the content the user accessed to compare the difference in biometric responses. For example, control circuitry 404 may identify that "The Conjuring" is a horror movie with similar average biometric responses as "It: Chapter One," based on the biometrics database. If the user accesses "The Conjuring," control circuitry 404 may compare the biometric response of user to scenes in "The Conjuring" to scenes in "It: Chapter One." If the user's heart rate is less in the former, control circuitry 404 may determine that the user's disorder has lessened in severity. If the user's heart rate is in the normal range again over several readings, control circuitry 404 may determine that the user's heart rate is no longer abnormal.

It is contemplated that the steps or descriptions of FIG. 13 may be used with any other embodiment of this disclosure. In addition, the steps and descriptions described in relation to FIG. 13 may be done in alternative orders or in parallel to further the purposes of this disclosure. For example, each of these steps may be performed in any order or in parallel or substantially simultaneously to reduce lag or increase the speed of the system or method. Any of these steps may also be skipped or omitted from the process. Furthermore, it should be noted that any of the devices or equipment discussed in relation to FIGS. 4-5 could be used to perform one or more of the steps in FIG. 13.

The processes discussed above are intended to be illustrative and not limiting. One skilled in the art would appreciate that the steps of the processes discussed herein may be omitted, modified, combined, and/or rearranged, and any additional steps may be performed without departing from the scope of the invention. More generally, the above disclosure is meant to be exemplary and not limiting. Only the claims that follow are meant to set bounds as to what the present invention includes. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

What is claimed is:

1. A method for recommending content based on biometric information, the method comprising:
    identifying content being consumed by a user on user equipment;
    determining a content type of the content;
    selecting, from a plurality of device enablement rules, a device enablement rule that corresponds to the content type, wherein the device enablement rule comprises content criteria for acquiring the biometric information;
    determining whether the content satisfies the content criteria of the device enablement rule;
    in response to determining that the content satisfies the content criteria:
        acquiring, from a biometric device, the biometric information;
        generating, for display on the user equipment, a content recommendation based on the biometric information, wherein generating, for display on the user equipment, the content recommendation based on the biometric information comprises:
            determining that the biometric information of the user is of a first response level;
            retrieving additional biometric information of the user from memory, wherein the additional biometric information is of a second response level different from the first response level;
            identifying a media asset that triggered a biometric response of the second response level; and
            selecting the media asset as the content recommendation.

2. The method of claim 1, further comprising determining that the biometric information of the user does not match an expected biometric response for the content, wherein the content recommendation is based on the determination that the biometric information does not match the expected biometric response.

3. The method of claim 1, wherein acquisition of the biometric information ceases when the content fails to satisfy the content criteria.

4. The method of claim 1, wherein determining whether the content satisfies the content criteria of the device enablement rule comprises:
    searching a social network based on an identifier of the content to identify a plurality of communications associated with the content;
    identifying a number of the communications that were received by the social network within a threshold period of time of a progression point of the content;
    determining whether the number of the communications exceeds a minimum number of communications indicative of popularity; and
    in response to determining the number of the communications exceeds the minimum number of communications, determining that a portion of the content corresponding to the progression point of the content satisfies the content criteria of the device enablement rule.

5. The method of claim 4, wherein acquiring, from the biometric device, the biometric information of the user comprises:
    storing a start time and an end time of the portion of the content; and
    acquiring the biometric information of the user while the progression point is between the start time and the end time.

6. The method of claim 1, further comprising:
    retrieving from the device enablement rule a set of biometric devices specified in the device enablement rule;
    retrieving a list of biometric devices associated with the user;
    comparing the list of biometric devices associated with the user with the set of biometric devices specified in the device enablement rule; and
    selecting as the biometric device one or more of the biometric devices in the list associated with the user that matches one or more of the biometric devices in the set of biometric devices.

7. The method of claim 1, wherein acquiring, from the biometric device, the biometric information of the user comprises:
    acquiring the biometric information of the user at a first progression point of the content;
    monitoring additional metadata of the content corresponding to a second progression point later than the first progression point;
    comparing the additional metadata to the content criteria of the device enablement rule;
    determining, based on the comparing, whether the content at the second progression point satisfies the content criteria of the device enablement rule; and
    in response to determining that the content at the second progression point does not satisfy the content criteria of the device enablement rule, ceasing acquisition of the biometric information of the user at the second progression point.

8. The method of claim 1, wherein acquiring the biometric information of the user occurs at a first progression point of the content, further comprising:
- retrieving an average biometric response of a plurality of users to the content being accessed at the first progression point;
- determining whether the biometric information of the user corresponds to the average biometric response;
- in response to determining that the biometric information of the user corresponds to the average biometric response, selecting as the content recommendation, a media asset indicated in a profile associated with at least one user of the plurality of users.

9. The method of claim 8, further comprising:
- in response to determining that the biometric information of the user does not correspond to the average biometric response, identifying a potential disorder related to an atypical biometric response to content that matches the content criteria; and
- alerting another user associated with the user about the potential disorder of the user.

10. A system for recommending content based on biometric information, the system comprising:
- control circuitry configured to:
  - identify content being consumed by a user on user equipment;
  - determine a content type of the content;
  - select, from a plurality of device enablement rules, a device enablement rule that corresponds to the content type, wherein the device enablement rule comprises content criteria for acquiring the biometric information;
  - determine whether the content satisfies the content criteria of the device enablement rule;
  - in response to determining that the content satisfies the content criteria:
    - acquire, from a biometric device, the biometric information of the user;
      - generate, for display on the user equipment, a content recommendation based on the biometric information, wherein to generate, for display on the user equipment, the content recommendation based on the biometric information the control circuitry is configured to:
        - determine that the biometric information of the user is of a first response level;
        - retrieve additional biometric information of the user from memory, wherein the additional biometric information is of a second response level different from the first response level;
        - identify a media asset that triggered a biometric response of the second response level; and
        - select the media asset as the content recommendation.

11. The system of claim 10, wherein the control circuitry is further configured to determine that the biometric information of the user does not match an expected biometric response for the content, and wherein the content recommendation is based on the determination that the biometric information does not match the expected biometric response.

12. The system of claim 10, wherein the control circuitry is further configured to cease acquisition of the biometric information when the content fails to satisfy the content criteria.

13. The system of claim 10, wherein to determine whether the content satisfies the content criteria of the device enablement rule the control circuitry is further configured to:
- search a social network based on an identifier of the content to identify a plurality of communications associated with the content;
- identify a number of the communications that were received by the social network within a threshold period of time of a progression point of the content;
- determine whether the number of the communications exceeds a minimum number of communications indicative of popularity; and
- in response to the determination that the number of the communications exceeds the minimum number of communications, determine that a portion of the content corresponding to the progression point of the content satisfies the content criteria of the device enablement rule.

14. The system of claim 13, wherein to acquire, from the biometric device, the biometric information of the user to the content while the content satisfies the content criteria the control circuitry is further configured to:
- store a start time and an end time of the portion of the content; and
- acquire the biometric information of the user while the progression point is between the start time and the end time.

15. The system of claim 10, wherein the control circuitry is further configured to:
- retrieve from the device enablement rule a set of biometric devices specified in the device enablement rule;
- retrieve a list of biometric devices associated with the user;
- compare the list of biometric devices associated with the user with the set of biometric devices specified in the device enablement rule; and
- select as the biometric device one or more of the biometric devices in the list associated with the user that matches one or more of the biometric devices in the set of biometric devices.

16. The system of claim 10, wherein to acquire, from the biometric device, the biometric information of the user to the content while the content satisfies the content criteria the control circuitry is further configured to:
- acquire the biometric information of the user at a first progression point of the content;
- monitor additional metadata of the content corresponding to a second progression point later than the first progression point;
- compare the additional metadata to the content criteria of the device enablement rule;
- determine, based on the comparing, whether the content at the second progression point satisfies the content criteria of the device enablement rule; and
- in response to the determination that the content at the second progression point does not satisfy the content criteria of the device enablement rule, cease acquisition of the biometric information of the user at the second progression point.

17. The system of claim 10, wherein to acquire the biometric information of the user at a first progression point of the content the control circuitry is further configured to:
- retrieve an average biometric response of a plurality of users to the content being accessed at the first progression point;
- determine whether the biometric information of the user corresponds to the average biometric response;

in response to the determination that the biometric information of the user corresponds to the average biometric response, select as the content recommendation, a media asset indicated in a profile associated with at least one user of the plurality of users.

18. The system of claim 17, wherein the control circuitry is further configured to:

in response to the determination that the biometric information of the user does not correspond to the average biometric response, identify a potential disorder related to an atypical biometric response to content that matches the content criteria; and alert another user associated with the user about the potential disorder of the user.

* * * * *